United States Patent
Poddutoori et al.

(10) Patent No.: US 8,470,878 B2
(45) Date of Patent: Jun. 25, 2013

(54) HETEROCYCLIC SULFONAMIDE DERIVATIVES

(75) Inventors: Ramulu Poddutoori, Bangalore (IN); Can Wang, Changshu (CN); Xianglin Zhao, Changshu (CN)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 13/491,205

(22) Filed: Jun. 7, 2012

(65) Prior Publication Data

US 2012/0316149 A1    Dec. 13, 2012

(30) Foreign Application Priority Data

Jun. 9, 2011  (IN) ............................... 1634/DEL/11

(51) Int. Cl.
A61K 31/343    (2006.01)
C07D 307/79    (2006.01)

(52) U.S. Cl.
USPC ........................................ 514/469; 549/471

(58) Field of Classification Search
USPC ................... 549/467, 471; 514/469
See application file for complete search history.

(56) References Cited

U.S. PATENT DOCUMENTS

| | | | |
|---|---|---|---|
| 7,045,539 | B2 | 5/2006 | Barlaam et al. |
| 7,199,147 | B2 | 4/2007 | Imazaki et al. |
| 7,465,815 | B2 | 12/2008 | Ohkawa et al. |
| 7,507,841 | B2 | 3/2009 | Ohkawa et al. |
| 2006/0106074 | A1 | 5/2006 | Bernstein et al. |
| 2007/0275984 | A1 | 11/2007 | Imogai et al. |

FOREIGN PATENT DOCUMENTS

| | | |
|---|---|---|
| WO | 2007/091106 A2 | 8/2007 |
| WO | 2008/089459 A1 | 7/2008 |
| WO | 2009/018238 A1 | 2/2009 |
| WO | 2009/019504 A1 | 2/2009 |
| WO | 2009/112490 A1 | 9/2009 |
| WO | 2010/145197 A1 | 12/2010 |
| WO | 2011/070030 A1 | 6/2011 |

OTHER PUBLICATIONS

Cancer [online], [retrieved on Jul. 6, 2007] Retrieved from the Internet, URL: http://www.nlm.nih.gov/medlineplus/cancer.html.*
Lala et al., Role of nitric oxide in tumor progression: Lessons from experimental tumors, Cancer and Metastasis Reviews (1998), 17, 91-106.*
Golub et al., Molecular Classification of Cancer: Class Discovery and Class Prediction by Gene Expression Monitoring, Science (1999), vol. 286, 531-537.*

* cited by examiner

*Primary Examiner* — Kristin Vajda
(74) *Attorney, Agent, or Firm* — Scott W. Reid

(57) ABSTRACT

The present invention relates to compounds:

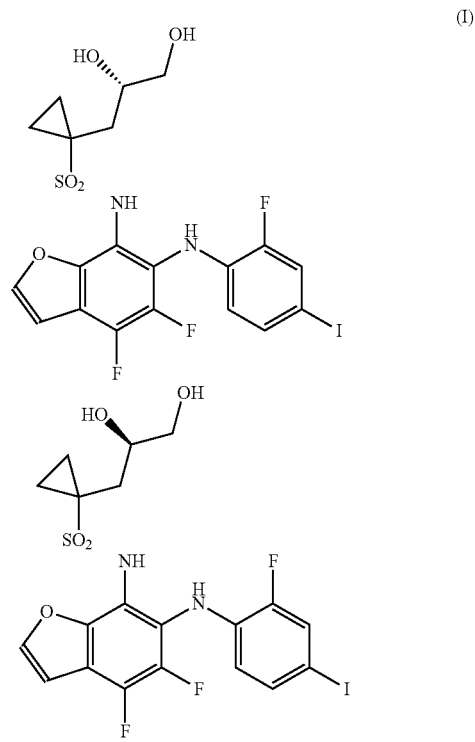

and pharmaceutically acceptable salts thereof. The compounds have been demonstrated as inhibitors of MEK and therefore may be useful in the treatment of hyperproliferative diseases like cancer and inflammation.

12 Claims, No Drawings

HETEROCYCLIC SULFONAMIDE DERIVATIVES

CROSS-REFERENCE TO RELATED APPLICATIONS

This application claims the benefit of priority to patent application 1634/DEL/11 filed in India on 9 Jun. 2011. The full disclosure of this application is incorporated herein by reference in its entirety and for all purposes.

FIELD OF THE INVENTION

The invention relates to heterocyclic sulfonamide compounds and pharmaceutical compositions thereof, in particular heterocyclic sulfonamide compounds that are specific inhibitors of kinase activity of MEK. The invention also relates to the use of the compounds and compositions thereof in the management of hyperproliferative diseases like cancer and inflammation.

BACKGROUND OF THE INVENTION

Hyperproliferative diseases like cancer and inflammation are receiving a lot of attention from the scientific community and there is a strong desire to discover compounds that provide therapeutic benefits with regard to treating hyperproliferative diseases. In this regard efforts have been made to identify and target specific mechanisms which play a role in proliferating the diseases.

One target of interest is the over-activation of mitogen-activated protein (MAP) kinase cascade which is known to play an important role in cell proliferation and differentiation. This pathway can be activated when a growth factor binds to its receptor tyrosine kinase. This interaction promotes RAS association with RAF and initiates a phosphorylation cascade through MEK (MAP kinase) to ERK Inhibition of this pathway is known to be beneficial in treating hyperproliferative diseases. MEK is an attractive therapeutic target because the only known substrates for MEK phosphorylation are the MAP kinases, ERK1 and ERK2. Constitutive activation of MEK/ERK was been found in pancreatic, colon, lung, kidney and ovarian primary tumor samples.

Phosphorylation of MEK appears to increase its affinity and its catalytic activity toward ERK as well as is affinity for ATP. This invention describes compounds that inhibit MEK activity by modulation of ATP binding, association of MEK with ERK by mechanisms that are competitive, and/or allosteric and/or uncompetitive.

Activation of MEK has been demonstrated in many disease models thus suggesting that inhibition of MEK could have potential therapeutic benefit in various diseases such as Pain (see, e.g., Evidence of efficacy in pain models described in *J. Neurosci.* 22:478, 2002; *Acta Pharmacol Sin.* 26:789 2005; *Expert Opin Ther Targets.* 9:699, 2005; and *Mol. Pain.* 2:2, 2006): Stroke (see, e.g., Evidence of efficacy in stroke models significant neuroprotection against ischemic brain injury by inhibition of the MEK described in *J. Pharmacol. Exp. Ther.* 304:172, 2003; and Brain Res. 996:55, 2004); Diabetes (see, e.g., Evidence in diabetic complications described in Am. J. Physiol. Renal. 286, F120 2004); Inflammation (see e.g., Evidence of efficacy in inflammation models described in *Biochem Biophy. Res. Com.* 268:647, 2000); and Arthritis (see, e.g, Evidence of efficacy in experimental osteoarthritis and arthritis as described in *J. Clin. Invest.* 116:163. 2006).

Although inhibition of MEK has been shown to have potential therapeutic benefit in several studies, there still remains a need to find compounds having commercial application.

SUMMARY OF THE INVENTION

The invention provides the compounds (S)—N-(4,5-difluoro-6-((2-fluoro-4-iodophenyl)amino)benzofuran-7-yl)-1-(2,3-dihydroxypropyl)cyclopropane-1-sulfonamide and (R)—N-(4,5-difluoro-6-((2-fluoro-4-iodophenyl)amino)benzofuran-7-yl)-1-(2,3-dihydroxypropyl)cyclopropane-1-sulfonamide:

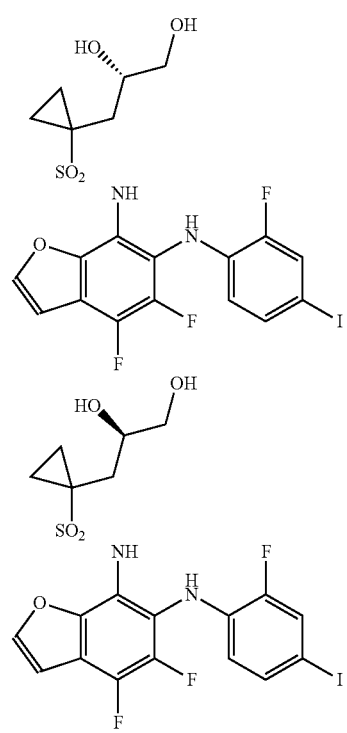

These compounds of the invention exist as isomeric configurations with chiral centers. Both isomeric forms are contemplated to be within the scope of the present invention. Each compound can be prepared as single isomers and/or separated into single isomers by techniques known to those skilled in the art. Therefore, the compounds of the present invention can be used in their single isomer or isomeric form. Also contemplated are the pharmaceutically acceptable salts thereof.

In another aspect of the present invention, a pharmaceutical composition is provided which comprises the compounds described above, or a pharmaceutically acceptable salt thereof, and a pharmaceutically acceptable excipient.

DEFINITIONS

Unless specified otherwise, the term "compound of the present invention" refers to (S)—N-(4,5-difluoro-6-((2-fluoro-4-iodophenyl)amino)benzofuran-7-yl)-1-(2,3-dihydroxypropyl)cyclopropane-1-sulfonamide or (R)—N-(4,5-difluoro-6-((2-fluoro-4-iodophenyl)amino)benzofuran-7-yl)-1-(2,3-dihydroxypropyl)cyclopropane-1-sulfonamide, and salts thereof, as well as all isotopically labeled compounds (including deuterium substitutions), and inherently formed moieties (e.g., polymorphs, solvates and/or hydrates).

DESCRIPTION OF PREFERRED EMBODIMENTS

The present invention provides compounds and pharmaceutical compositions thereof that are useful in the treatment of diseases, conditions and/or disorders modulated by the inhibition of kinase activity of MEK.

Compounds of the present invention may be synthesized by synthetic routes that include processes analogous to those well-known in the chemical arts, particularly in light of the description contained herein. The starting materials are generally available from commercial sources such as Aldrich Chemicals (Milwaukee, Wis.) or are readily prepared using methods well known to those skilled in the art (e.g., prepared by methods generally described in Louis F. Fieser and Mary Fieser, Reagents for Organic Synthesis, v. 1-19, Wiley, New York (1967-1999 ed.), or Beilsteins Handbuch der organischen Chemie, 4, Aufl. ed. Springer-Verlag, Berlin, including supplements (also available via the Beilstein online database)).

For a detailed description of the individual reaction steps, see the Examples section below. Those skilled in the art will appreciate that other synthetic routes may be used to synthesize the inventive compound. Although specific starting materials and reagents are described, those of skill in the art will appreciate that other starting materials and reagents can be easily substituted to provide a variety of derivatives and/or reaction conditions.

Compounds of the invention are capable of forming salts with bases, in particular pharmaceutically acceptable bases such as those well known in the art; suitable such salts include metal salts, particularly alkali metal or alkaline earth metal salts such as sodium, potassium, magnesium or calcium salts, or salts with ammonia or pharmaceutically acceptable organic amines or heterocyclic bases such as ethanolamines, benzylamines or pyridine. These salts may be prepared by known salt-forming procedures.

The present invention includes isotopically-labeled or -enriched compounds of the present invention. Representative examples of isotopes suitable for inclusion in the compounds of the invention include isotopes of hydrogen, such as $^2$H and $^3$H, carbon, such as $^{11}$C, $^{13}$C and $^{14}$C, chlorine, such as $^{36}$Cl, fluorine, such as $^{18}$F, iodine, such as $^{123}$I and $^{125}$I, nitrogen, such as $^{13}$N and $^{15}$N, oxygen, such as $^{15}$O, $^{17}$O and $^{18}$O, phosphorus, such as $^{32}$P, and sulphur, such as $^{35}$S.

Substitution with heavier isotopes such as deuterium, i.e. $^2$H, may afford certain therapeutic advantages resulting from greater metabolic stability, for example, increased in vivo half-life or reduced dosage requirements, and hence may be preferred in some circumstances.

Isotopically-labeled compounds of the present invention can generally be prepared by conventional techniques known to those skilled in the art or by processes analogous to those described in the accompanying Examples and Preparations Sections using an appropriate isotopically-labeled reagent in place of the non-labeled reagent previously employed.

The compounds of the present invention may exist in unsolvated as well as solvated forms with pharmaceutically acceptable solvents such as water, ethanol, and the like, and it is intended that the invention embrace both solvated and unsolvated forms. For purposes of the present invention, solvates (including hydrates) are considered pharmaceutical compositions, e.g., a compound of the present invention in combination with an excipient, wherein the excipient is a solvent.

The present invention also relates to a pharmaceutical composition comprising a compound of the present invention and a pharmaceutically acceptable excipient.

Suitable excipients generally include corn starch, potato starch, tapioca starch, starch paste, pre-gelatinized starch, sugars, gelatin, natural gums, synthetic gums, sodium alginate, alginic acid, tragacanth, guar gum, cellulose, ethyl cellulose, cellulose acetate, carboxymethyl cellulose calcium, sodium carboxymethylcellulose, methyl cellulose, hydroxypropyl methylcellulose, microcrystalline cellulose, magnesium aluminum silicate, polyvinyl pyrrolidone, talc, calcium carbonate, powdered cellulose, dextrates, kaolin, mannitol, silicic acid, sorbitol, agar-agar, sodium carbonate, croscarmellose sodium, crospovidone, polacrilin potassium, sodium starch glycolate, clays, sodium stearate, calcium stearate, magnesium stearate, stearic acid, mineral oil, light mineral oil, glycerin, sorbitol, mannitol, polyethylene glycol, other glycols, sodium lauryl sulfate, hydrogenated vegetable oil, peanut oil, cottonseed oil, sunflower oil, sesame oil, olive oil, corn oil, soybean oil, zinc stearate, sodium oleate, ethyl oleate, ethyl laureate, silica, and combinations thereof.

A typical formulation is prepared by mixing a compound of the present invention and a carrier, diluent or excipient. Suitable carriers, diluents and excipients are well known to those skilled in the art and include materials such as carbohydrates, waxes, water soluble and/or swellable polymers, hydrophilic or hydrophobic materials, gelatin, oils, solvents, water, and the like. The particular carrier, diluent or excipient used will depend upon the means and purpose for which the compound of the present invention is being applied. Solvents are generally selected based on solvents recognized by persons skilled in the art as safe (GRAS) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG400, PEG300), etc. and mixtures thereof. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound of the present invention or pharmaceutical composition thereof) or aid in the manufacturing of the pharmaceutical product (i.e., medicament).

The formulations may be prepared using conventional dissolution and mixing procedures. For example, the bulk drug substance (i.e., compound of the present invention or stabilized form of the compound (e.g., complex with a cyclodextrin derivative or other known complexation agent)) is dissolved in a suitable solvent in the presence of one or more of the excipients. The compound of the present invention is typically formulated into pharmaceutical dosage forms to provide an easily controllable dosage of the drug and to give the patient an elegant and easily handleable product.

The composition is generally formulated into various dosage forms selected from a group comprising tablet, troches, lozenges, aqueous or oily suspensions, ointment, patch, gel, lotion, dentifrice, capsule, emulsion, creams, spray, drops, dispersible powders or granules, emulsion in hard or soft gel capsules, syrups and elixirs.

The pharmaceutical composition (or formulation) for application may be packaged in a variety of ways depending upon the method used for administering the drug. Generally, an article for distribution includes a container having deposited therein the pharmaceutical formulation in an appropriate form. Suitable containers are well-known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

The compounds of the present invention are useful as both prophylactic and therapeutic treatments for diseases or conditions related to the hyperactivity of MEK, as well as diseases or conditions modulated by the Raf/Ras/Mek pathway.

Thus, as a further aspect, the invention relates to a method for treating a disease or condition related to the hyperactivity of MEK, or a disease or condition modulated by the MEK cascade, comprising administration of an effective therapeutic amount of a compound of the present invention.

As a further aspect, the invention relates to a method for treating proliferative diseases, such as cancer, comprising administration of an effective amount of a compound of the present invention.

Examples of cancers include but are not limited to: angiosarcoma, fibrosarcoma, rhabdomyosarcoma, liposarcoma, myxoma, rhabdomyoma, fibroma, lipoma, teratoma; bronchogenic carcinoma, squamous cell carcinoma, undifferentiated small cell carcinoma, undifferentiated large cell carcinoma, alveolar (bronchiolar) carcinoma, bronchial adenoma, lymphoma, chondromatous hanlartoma, inesothelioma, esophageal squamous cell carcinoma, leiomyosarcoma, leiomyosarcoma, ductal adenocarcinoma, insulinorna, glucagonoma, gastrinoma, vipoma, stomach and small bowel carcinoid tumors, adenocarcinoma, Karposi's sarcoma, leiomyoma, hemangioma, lipoma, neurofibroma, fibroma, tubular adenoma, villous adenoma, hamartoma, Wilm's tumor [nephroblastoma, leukemia, bladder and urethra squamous cell carcinoma, transitional cell carcinoma, adenocarcinoma, seminoma, teratoma, embryonal carcinoma, teratocareinoma, choriocarcinoma, interstitial cell carcinoma, fibroadenoma, adenomatoid tumors, hepatoma (hepatocellular carcinoma), cholangiocarcinoma, hepatoblastoma, hepatocellular adenoma, hemangioma, osteogenic sarcoma (osteosarcoma), malignant fibrous histiocytoma, chondrosarcoma, Ewing's sarcoma, malignant lyinphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors, osteoma, granuloma, xanthoma, osteitis deformians, meningioma, meningiosarcoma, gliomatosis, astrocytoma, medulloblastoma, glioma, ependymoma, germinoma [pinealoma], glioblastoma multiform, oligodendroglioma, schwannoma, retinoblastoma, congenital tumors, spinal cord neurofibroma, meningioma, glioma, endometrial carcinoma, cervical carcinoma, pre-tumor cervical dysplasia, ovarian carcinoma, serous cystadenocarcinoma, mucinous cystadenocarcinoma, granulosa-thecal cell tumors, Sertoli-Leydig cell tumors, dysgerminoma, malignant teratoma, intraepithelial carcinoma, adenocarcinoma, melanoma), vaginal clear cell carcinoma, botryoid sarcoma (embryonal rhabdomyosarcoma), fallopian tube carcinoma, acute and chronic myeloid leukemia, acute lymphoblastic leukemia, chronic lymphocytic leukemia, myeloproliferative diseases, multiple myeloma, myelodysplastic syndrome, Hodgkin's disease, non-Hodgkin's lymphoma, malignant lymphoma, malignant melanoma, basal cell carcinoma, moles, dysplastic nevi, angioma, dermatofibroma, keloids, psoriasis, and neuroblastoma.

The present invention includes a method of treating cancer selected from non-small cell lung carcinoma, pancreatic carcinoma, bladder carcinoma, colon carcinoma, myeloid disorders, breast cancer, prostate cancer, thyroid cancer, melanoma, adenomas and carcinomas of the ovary, eye, liver, biliary tract, and nervous system and advanced solid tumors with KRAS, NRAS and BRAF mutations, comprising administering to a subject in need of such treatment an effective amount of a compound of the invention.

The compounds of the present invention may also be useful in the treatment of other diseases or conditions related to the hyperactivity of MEK. Thus, as a further aspect, the invention relates to a method of treatment of a disorder selected from: xenograft (cellos), skin, limb, organ or bone marrow transplant) rejection; osteoarthritis; rheumatoid arthritis; cystic fibrosis; complications of diabetes (including diabetic retinopathy and diabetic nephropathy); hepatomegaly; cardiomegaly; stroke (such as acute focal ischemic stroke and global cerebral ischemia); heart failure; septic shock; asthma; chronic obstructive pulmonary disorder; Alzheimer's disease; and chronic or neuropathic pain.

The term "chronic pain" for purposes of the present invention includes, but is not limited to, idiopathic pain, and pain associated with chronic alcoholism, vitamin deficiency, uremia, or hypothyroidism. Chronic pain is associated with numerous conditions including, but not limited to, inflammation, and post-operative pain.

As used herein, the term "neuropathic pain" is associated with numerous conditions which include, but are not limited to, inflammation, postoperative pain, phantom limb pain, burn pain, gout, trigeminal neuralgia, acute herpetic and postherpetic pain, causalgia, diabetic neuropathy, plexus avulsion, neuroma, vasculitis, viral infection, crush injury, constriction injury, tissue injury, limb amputation, and nerve injury between the peripheral nervous system and the central nervous system.

Compounds of the present invention may also be useful as antiviral agents for treating viral infections such as HIV, hepatitis (B) virus (HBV) human papilloma virus (HPV), cytomegalovirus (CMV), and Epstein-Barr virus (EBV).

Compounds of the present invention may also be useful in the treatment of restenosis, psoriasis, allergic contact dermatitis, autoimmune disease, atherosclerosis and inflammatory bowel diseases, e.g. Crohn's disease and ulcerative colitis.

A MEK inhibitor of the present invention may be usefully combined with another pharmacologically active compound (additional therapeutic agent), or with two or more other pharmacologically active compounds, particularly in the treatment of cancer. For example, a compound of the present invention, as defined above, may be administered simultaneously, sequentially or separately in combination with one or more additional therapeutic agents selected from an anticancer drug (or chemotherapy agent), a pain medication, an antiemetic, an antidepressant or an anti-inflammatory agent. Chemotherapy agents include, for example, mitotic inhibitors such as a taxane, a vinca alkaloid, paclitaxel, docetaxel, vincristine, vinblastine, vinorelbine or vinflunine, and other anticancer agents, e.g. cisplatin, 5-fluorouracil or 5-fluoro-2-4 (1H,3H)-pyrimidinedione (5FU), flutamide or gemcitabine.

Such combinations may offer significant advantages, including synergistic activity, in therapy.

A compound of the present invention may also be used to advantage in combination with other antiproliferative compounds. Such antiproliferative compounds include, but are not limited to aromatase inhibitors; antiestrogens; topoisomerase I inhibitors; topoisomerase II inhibitors; microtubule active compounds; alkylating compounds; histone deacetylase inhibitors, such as LBH589; compounds which induce cell differentiation processes; cyclooxygenase inhibitors; MMP inhibitors; mTOR inhibitors, such as RAD001; antineoplastic antimetabolites; platin compounds; compounds targeting/decreasing a protein or lipid kinase activity and further anti-angiogenic compounds; compounds which target, decrease or inhibit the activity of a protein or lipid phosphatase; gonadorelin agonists; anti-androgens; methionine aminopeptidase inhibitors; bisphosphonates; biological response modifiers; antiproliferative antibodies; heparanase inhibitors; inhibitors of Ras oncogenic isoforms; telomerase inhibitors; proteasome inhibitors; compounds used in the treatment of hematologic malignancies; compounds which target, decrease or inhibit the activity of Flt-3, such as PKC412; Hsp90 inhibitors such as 17-AAG (17-allylamino-gelda-namycin, NSC330507), 17-DMAG (17-dimethylaminoethylamino-17-demethoxy-geldana-mycin, NSC707545), IPI-504, CNF1010, CNF2024, CNF1010 from Conforma Therapeutics and AUY922; temozolomide (TEMODAL); kinesin spindle protein inhibitors, such as SB715992 or SB743921 from GlaxoSmithKline, or pentamidine/chlorpromazine from CombinatoRx; PI3K inhibitors, such as BEZ235; RAF inhibitors, such as RAF265 and LGX818; EDG binders, antileukemia compounds, ribonucleotide reductase inhibitors, S-adenosylmethionine decarboxylase inhibitors, antiproliferative anti-bodies or other chemotherapeutic compounds. Further, alternatively or in addition they may be used in combination with other tumor treatment approaches, including surgery, ionizing radiation, photodynamic therapy, implants, e.g. with corticosteroids, hormones, or they may be used as radiosensitizers. Also, in anti-inflammatory and/or antiproliferative treatment, combination with anti-inflammatory drugs is included. Combination is also possible with antihistamine drug substances, bronchodilatatory drugs, NSAID or antagonists of chemokine receptors.

The term "aromatase inhibitor" as used herein relates to a compound which inhibits the estrogen production, i.e. the conversion of the substrates androstenedione and testosterone to estrone and estradiol, respectively. The term includes, but is not limited to steroids, especially atame-stane, exemestane and formestane and, in part-icular, non-steroids, especially aminoglutethimide, roglethimide, pyridoglutethimide, trilostane, testolactone, ketoconazole, vorozole, fadrozole, anastrozole and letrozole. Exemestane can be administered, e.g., in the form as it is marketed, e.g. under the trademark AROMASIN. Formestane can be administered, e.g., in the form as it is marketed, e.g. under the trademark LENTARON. Fadrozole can be administered, e.g., in the form as it is marketed, e.g. un-der the trademark AFEMA. Anastrozole can be administered, e.g., in the form as it is marketed, e.g. under the trademark ARIMIDEX. Letrozole can be administered, e.g., in the form as it is marketed, e.g. under the trademark FEMARA or FEMAR. Amino glutethimide can be administered, e.g., in the form as it is marketed, e.g. under the trademark, ORIMETEN. A combination of the invention comprising a chemo-therapeutic agent which is an aromatase inhibitor is particularly useful for the treatment of hormone receptor positive tumors, e.g., breast tumors.

The term "anti-estrogen" as used herein relates to a compound which antagonizes the effect of estrogens at the estrogen receptor level. The term includes, but is not limited to tamoxifen, fulvestrant, raloxifene and raloxifene hydrochloride. Tamoxifen can be administered, e.g., in the form as it is marketed, e.g. under the trademark NOLVADEX. Raloxifene hydrochloride can be administered, e.g., in the form as it is marketed, e.g. under the trademark EVISTA. Fulvestrant can be formulated as disclosed in U.S. Pat. No. 4,659,516 or it can be administered, e.g., in the form as it is marketed, e.g. under the trademark FASLODEX. A combination of the invention comprising a chemotherapeutic agent which is an anti-estrogen is particularly useful for the treatment of estrogen receptor positive tumors, e.g. breast tumors.

The term "anti-androgen" as used herein relates to any substance which is capable of in-hibiting the biological effects of androgenic hormones and includes, but is not limited to, bicalutamide (CASODEX), which can be formulated, e.g. as disclosed in U.S. Pat. No. 4,636,505.

The term "gonadorelin agonist" as used herein includes, but is not limited to abarelix, goserelin and goserelin acetate. Goserelin is disclosed in U.S. Pat. No. 4,100,274 and can be administered, e.g., in the form as it is marketed, e.g. under the trademark ZOLADEX. Abarelix can be formulated, e.g. as disclosed in U.S. Pat. No. 5,843,901.

The term "topoisomerase I inhibitor" as used herein includes, but is not limited to topotecan, gimatecan, irinotecan, camptothecin and its analogues, 9-nitrocamptothecin and the macromolecular camptothecin conjugate PNU-166148 (compound A1 in WO99/17804). Irinotecan can be administered, e.g. in the form as it is marketed, e.g. under the trademark CAMPTOSAR. Topotecan can be administered, e.g., in the form as it is marketed, e.g. under the trademark HYCAMTIN.

The term "topoisomerase II inhibitor" as used herein includes, but is not limited to the an-thracyclines such as doxorubicin (including liposomal formulation, e.g. CAELYX), daunorubicin, epirubicin, idarubicin and nemorubicin, the anthraquinones mitoxantrone and losoxantrone, and the podophillotoxines etoposide and teniposide. Etoposide can be administered, e.g. in the form as it is marketed, e.g. under the trademark ETOPOPHOS. Teniposide can be administered, e.g. in the form as it is marketed, e.g. under the trademark VM 26-BRISTOL. Doxorubicin can be administered, e.g. in the form as it is marketed, e.g. under the trademark ADRIBLASTIN or ADRIAMYCIN. Epirubicin can be administered, e.g. in the form as it is marketed, e.g. under the trademark FARMORUBICIN. Idarubicin can be administered, e.g. in the form as it is marketed, e.g. under the trademark ZAVEDOS. Mitoxantrone can be administered, e.g. in the form as it is marketed, e.g. under the trademark NOVANTRON.

The term "microtubule active compound" relates to microtubule stabilizing, microtubule destabilizing compounds and microtublin polymerization inhibitors including, but not limited to taxanes, e.g. paclitaxel and docetaxel, vinca alkaloids, e.g., vinblastine, especially vinblastine sulfate, vincristine especially vincristine sulfate, and vinorelbine, discodermolides, cochicine and epothilones and derivatives thereof, e.g. epothilone B or D or derivatives thereof. Paclitaxel may be administered e.g. in the form as it is marketed, e.g. TAXOL. Docetaxel can be administered, e.g., in the form as it is marketed, e.g. under the trademark TAXOTERE. Vinblastine sulfate can be administered, e.g., in the form as it is marketed, e.g. under the trademark VINBLASTIN R.P. Vincristine sulfate can be administered, e.g., in the form as it is marketed, e.g. under the trademark FARMISTIN. Discodermolide can be obtained, e.g., as disclosed in U.S. Pat. No. 5,010,099. Also included are Epothilone derivatives which are disclosed in WO 98/10121, U.S. Pat. No. 6,194,181, WO 98/25929, WO 98/08849, WO 99/43653, WO 98/22461 and WO 00/31247. Especially preferred are Epothilone A and/or B.

The term "alkylating compound" as used herein includes, but is not limited to, cyclophosphamide, ifosfamide, melphalan or nitrosourea (BCNU or Gliadel). Cyclophosphamide can be administered, e.g., in the form as it is marketed, e.g. under the trademark CYCLOSTIN. Ifosfamide can be administered, e.g., in the form as it is marketed, e.g., under the trademark HOLOXAN.

The term "histone deacetylase inhibitors" or "HDAC inhibitors" relates to compounds which inhibit the histone deacetylase and which possess antiproliferative activity. This includes compounds such as sodium butyrate, LDH589 disclosed in WO 02/22577, especially N-hydroxy-3-[4-[[(2-hydroxyethyl)[2-(1H-indol-3-yl)ethyl]-amino]methyl]phenyl]-2E-2-propenamide, N-hydroxy-3-[4-[[[2-(2-methyl-1H-indol-3-yl)-ethyl]amino]methyl]phenyl]-2E-2-propenamide and pharmaceutically acceptable salts thereof, especially the lactate salt. It further especially includes suberoylanilide hydroxamic acid (SAHA), MS275, FK228 (formerly FR901228), trichostatin A and compounds disclosed in U.S. Pat. No. 6,552,065, in particular, N-hydroxy-3-[4-[[[2-(2-methyl-1H-indol-3-yl)-ethyl]-amino]-methyl]phenyl]-2E-2-propenamide, or a pharmaceutically acceptable salt thereof.

The term "antineoplastic antimetabolite" includes, but is not limited to, 5-Fluorouracil or 5-FU, capecitabine, gemcitabine, DNA demethylating compounds, such as 5-azacy-tidine and decitabine, methotrexate and edatrexate, and folic acid antagonists such as pemetrexed. Capecitabine can be administe-red, e.g., in the form as it is marketed, e.g. under the trademark XELODA. Gemcitabine can be administered, e.g., in the form as it is marketed, e.g. under the trademark GEMZAR.

The term "platin compound" as used herein includes, but is not limited to, carboplatin, cis-platin, cisplatinum and oxali-platin. Carboplatin can be administered, e.g., in the form as it is marketed, e.g. under the trademark CARBOPLAT. Oxaliplatin can be administered, e.g., in the form as it is marketed, e.g. under the trademark ELOXATIN.

The term "compounds targeting/decreasing a protein or lipid kinase activity"; or a "protein or lipid phosphatase activity"; or "further anti-angiogenic compounds" as used herein includes, but is not limited to, protein tyrosine kinase and/or serine and/or threonine kinase inhibitors or lipid kinase inhibitors, e.g., a) compounds targeting, decreasing or inhibiting the activity of the platelet-derived growth factor-receptors (PDGFR), such as compounds which target, decrease or inhibit the activity of PDGFR, especially compounds which inhibit the PDGF receptor, e.g. a N-phenyl-2-pyrimidine-amine derivative, e.g. imatinib, SU101, SU6668 and GFB-111;

b) compounds targeting, decreasing or inhibiting the activity of the fibroblast growth factor-receptors (FGFR);

c) compounds targeting, decreasing or inhibiting the activity of the insulin-like growth factor receptor I (IGF-IR), such as compounds which target, decrease or inhibit the activity of IGF-IR, especially compounds which inhibit the kinase activity of IGF-I receptor, such as those compounds disclosed in WO 02/092599, or antibodies that target the extracellular domain of IGF-I receptor or its growth factors;

d) compounds targeting, decreasing or inhibiting the activity of the Trk receptor tyrosine kinase family, or ephrin B4 inhibitors;

e) compounds targeting, decreasing or inhibiting the activity of the Axl receptor tyrosine kinase family;

f) compounds targeting, decreasing or inhibiting the activity of the Ret receptor tyrosine kinase;

g) compounds targeting, decreasing or inhibiting the activity of the Kit/SCFR receptor tyrosine kinase, i.e C-kit receptor tyrosine kinases—(part of the PDGFR family), such as compounds which target, decrease or inhibit the activity of the c-Kit receptor tyrosine kinase family, especially compounds which inhibit the c-Kit receptor, e.g. imatinib;

h) compounds targeting, decreasing or inhibiting the activity of members of the c-Abl family, their gene-fusion products (e.g. BCR-Abl kinase) and mutants, such as com-pounds which target decrease or inhibit the activity of c-AbI family members and their gene fusion products, e.g. a N-phenyl-2-pyrimidine-amine derivative, e.g. imatinib or nilotinib (AMN107); PD180970; AG957; NSC 680410; PD173955 from ParkeDavis; or dasatinib (BMS-354825);

i) compounds targeting, decreasing or inhibiting the activity of members of the protein kinase C(PKC) and Raf family of serine/threonine kinases, members of the MEK, SRC, JAK, FAK, PDK1, PKB/Akt, and Ras/MAPK family members, and/or members of the cyclin-dependent kinase family (CDK) and are especially those staurosporine derivatives disclosed in U.S. Pat. No. 5,093,330, e.g. midostaurin; examples of further compounds include e.g. UCN-01, safingol, BAY 43-9006, Bryostatin 1, Perifosine; Ilmofosine; RO 318220 and RO 320432; GO 6976; Isis 3521; LY333531/LY379196; isochinoline compounds such as those disclosed in WO 00/09495; FTIs; BEZ235 (a P13K inhibitor) or AT7519 (CDK inhibitor);

j) compounds targeting, decreasing or inhibiting the activity of protein-tyrosine kinase inhibitors, such as compounds which target, decrease or inhibit the activity of protein-tyrosine kinase inhibitors include imatinib mesylate (GLEEVEC) or tyrphostin. A tyrphostin is preferably a low molecular weight (mw<1500) compound, or a pharmaceutically acceptable salt thereof, especially a compound selected from the benzylidenemalonitrile class or the S-arylbenzenemalonirile or bisubstrate quinoline class of compounds, more especially any compound selected from the group consisting of Tyrphostin A23/RG-50810; AG 99; Tyrphostin AG 213; Tyrphostin AG 1748; Tyrphostin AG 490; Tyrphostin B44; Tyrphostin B44 (+) enantiomer; Tyrphostin AG 555; AG 494; Tyrphostin AG 556, AG957 and adaphostin (4-{[(2,5-dihydroxyphenyl)methyl]amino}-benzoic acid adamantyl ester; NSC 680410, adaphostin);

k) compounds targeting, decreasing or inhibiting the activity of the epidermal growth factor family of receptor tyrosine kinases (EGFR, ErbB2, ErbB3, ErbB4 as homo- or heterodimers) and their mutants, such as compounds which target, decrease or inhibit the activity of the epidermal growth factor receptor family are especially compounds, proteins or antibodies which inhibit members of the EGF receptor tyrosine kinase family, e.g. EGF receptor, ErbB2, ErbB3 and ErbB4 or bind to EGF or EGF related ligands, and are in particular those compounds, proteins or monoclonal antibodies generically and specifically disclosed in WO 97/02266, e.g. the compound of ex. 39, or in EP 0 564 409, WO 99/03854, EP 0520722, EP 0 566 226, EP 0 787 722, EP 0 837 063, U.S. Pat. No. 5,747,498, WO 98/10767, WO 97/30034, WO 97/49688, WO 97/38983 and, especially, WO 96/30347 (e.g. compound known as CP 358774), WO 96/33980 (e.g. compound ZD 1839) and WO 95/03283 (e.g. compound ZM105180); e.g. trastuzumab (Herceptin), cetuximab (Erbitux), Iressa, Tarceva, OSI-774, CI-1033, EKB-569, GW-2016, E1.1, E2.4, E2.5, E6.2, E6.4, E2.11, E6.3 or E7.6.3, and 7H-pyrrolo-[2,3-d]pyrimidine derivatives which are disclosed in WO 03/013541; and l) compounds targeting, decreasing or inhibiting the activity of the c-Met receptor, such as compounds which target, decrease or inhibit the activity of c-Met, especially compounds which inhibit the kinase activity of c-Met receptor, or antibodies that target the extracellular domain of c-Met or bind to HGF.

Further anti-angiogenic compounds include compounds having another mechanism for their activity, e.g. unrelated to protein or lipid kinase inhibition e.g. thalidomide (THALOMID) and TNP-470.

Compounds which target, decrease or inhibit the activity of a protein or lipid phosphatase are e.g., inhibitors of phosphatase 1, phosphatase 2A, or CDC25, e.g. okadaic acid or a derivative thereof.

Compounds which induce cell differentiation processes are e.g. retinoic acid, or tocopherol or tocotrienol.

The term cyclooxygenase inhibitor as used herein includes, but is not limited to, e.g. Cox-2 inhibitors, 5-alkyl substituted 2-arylaminophenylacetic acid and derivatives, such as celecoxib (CELEBREX), rofecoxib (VIOXX), etoricoxib, valdecoxib or a 5-alkyl-2-arylaminophenylacetic acid, e.g. 5-methyl-2-(2'-chloro-6'-fluoroanilino)phenyl acetic acid, lumiracoxib.

The term "bisphosphonates" as used herein includes, but is not limited to, etridonic, clodronic, tiludronic, pamidronic, alendronic, ibandronic, risedronic and zoledronic acid. "Etridonic acid" can be administered, e.g., in the form as it is marketed, e.g. under the trademark DIDRONEL. "Clodronic acid" can be administered, e.g., in the form as it is marketed, e.g. under the trademark BONEFOS. "Tiludronic acid" can be administered, e.g., in the form as it is marketed, e.g. under the trademark SKELID. "Pamidronic acid" can be administered, e.g. in the form as it is marketed, e.g. under the trademark AREDIA. "Alendronic acid" can be administered, e.g., in the form as it is marketed, e.g. under the trademark FOSAMAX. "Ibandronic acid" can be administered, e.g., in the form as it is marketed, e.g. under the trademark BONDRANAT. "Risedronic acid" can be administered, e.g., in the form as it is marketed, e.g. under the trademark ACTONEL. "Zoledronic acid" can be administered, e.g. in the form as it is marketed, e.g. under the trademark ZOMETA.

The term "mTOR inhibitors" relates to compounds which inhibit the mammalian target of rapamycin (mTOR) and which possess antiproliferative activity such as sirolimus (Rapamune), everolimus (CerticanO), CCI-779 and ABT578.

The term "heparanase inhibitor" as used herein refers to compounds which target, decrease or inhibit heparin sulfate degradation. The term includes, but is not limited to, PI-88.

The term "biological response modifier" as used herein refers to a lymphokine or interferons, e.g. interferon.

The term "inhibitor of Ras oncogenic isoforms", e.g. H-Ras, K-Ras, or N-Ras, as used herein refers to compounds which target, decrease or inhibit the oncogenic activity of Ras e.g. a "farnesyl transferase inhibitor" e.g. L-744832, DK8G557 or R115777 (Zarnestra).

The term "telomerase inhibitor" as used herein refers to compounds which target, decrease or inhibit the activity of telomerase. Compounds which target, decrease or inhibit the activity of telomerase are especially compounds which inhibit the telomerase receptor, e.g. telomestatin.

The term "methionine aminopeptidase inhibitor" as used herein refers to compounds which target, decrease or inhibit the activity of methionine aminopeptidase. Compounds which target, decrease or inhibit the activity of methionine aminopeptidase are e.g. bengamide or a derivative thereof.

The term "proteasome inhibitor" as used herein refers to compounds which target, decrease or inhibit the activity of the proteasome. Compounds which target, decrease or inhibit the activity of the proteasome include e.g. Bortezomid (Velcade) and MLN 341.

The term "matrix metalloproteinase inhibitor" or ("MMP" inhibitor) as used herein includes, but is not limited to, collagen peptidomimetic and nonpeptidomimetic inhibitors, tetracycline derivatives, e.g. hydroxamate peptidomimetic inhibitor batimastat and its orally bioavailable analogue marimastat (BB-2516), prinomastat (AG3340), metastat (NSC 683551) BMS-279251, BAY 12-9566, TAA211, MMI270B or AAJ996.

The term "compounds used in the treatment of hematologic malignancies" as used herein includes, but is not limited to, FMS-like tyrosine kinase inhibitors e.g. compounds targeting, decreasing or inhibiting the activity of FMS-like tyrosine kinase receptors (Flt-3R); interferon, 1-b-D-arabinofuransylcytosine (ara-c) and bisulfan; and ALK inhibitors e.g. compounds which target, decrease or inhibit anaplastic lymphoma kinase.

Compounds which target, decrease or inhibit the activity of FMS-like tyrosine kinase receptors (Flt-3R) are especially compounds, proteins or antibodies which inhibit members of the Flt-3R receptor kinase family, e.g. PKC412, TKI258, midostaurin, a staurosporine derivative, SU11248 and MLN518.

The term "HSP90 inhibitors" as used herein includes, but is not limited to, compounds targeting, decreasing or inhibiting the intrinsic ATPase activity of HSP90; degrading, targeting, decreasing or inhibiting the HSP90 client proteins via the ubiquitin proteosome pathway. Compounds targeting, decreasing or inhibiting the intrinsic ATPase activity of HSP90 are especially compounds, proteins or antibodies which inhibit the ATPase activity of HSP90 e.g., 17-allylamino,17-demethoxygeldanamycin (17AAG), a geldanamycin derivative; other geldanamycin related compounds, and radicicol.

The term "antiproliferative antibodies" as used herein includes, but is not limited to, trastuzumab (Herceptin), Trastuzumab-DM1,erbitux, bevacizumab (Avastin), rituximab (Rituxan), PRO64553 (anti-CD40) and 2C4 Antibody. By antibodies is meant e.g. intact monoclonal antibodies, polyclonal antibodies, multispe-cific antibodies formed from at least 2 intact antibodies, and antibodies fragments so long as they exhibit the desired biological activity.

For the treatment of acute myeloid leukemia (AML), compounds of formula (I) can be used in combination with standard leukemia therapies, especially in combination with therapies used for the treatment of AML. In particular, compounds of formula (I) can be administered in combination with, e.g., farnesyl transferase inhibitors and/or other drugs useful for the treatment of AML, such as Daunorubicin, Adriamycin, Ara-C, VP-16, Teniposide, Mitoxantrone, Idarubicin, Carboplatinum and PKC412.

The term "antileukemic compounds" includes, for example, Ara-C, a pyrimidine analog, which is the 2-alpha-hydroxy ribose (arabinoside) derivative of deoxycytidine. Also included is the purine analog of hypoxanthine, 6-mercaptopurine (6-MP) and fludarabine phosphate.

Somatostatin receptor antagonists as used herein refers to compounds which target, treat or inhibit the somatostatin receptor such as octreotide, and SOM230 (pasireotide).

Tumor cell damaging approaches refer to approaches such as ionizing radiation. The term "ionizing radiation" referred to above and hereinafter means ionizing radiation that occurs as either electromagnetic rays (such as X-rays and gamma rays) or particles (such as alpha and beta particles). Ionizing radiation is provided in, but not limited to, radiation therapy and is known in the art. See Hellman, Principles of Radiation Therapy, Cancer, in Principles and Practice of Oncology, Devita et al., Eds., 4th Edition, Vol. 1, pp. 248-275 (1993).

The term "EDG binders" as used herein refers a class of immunosuppressants that modulates lymphocyte recirculation, such as FTY720.

The term "ribonucleotide reductase inhibitors" refers to pyrimidine or purine nucleoside analogs including, but not limited to, fludarabine and/or cytosine arabinoside (ara-C), 6-thioguanine, 5-fluorouracil, cladribine, 6-mercaptopurine (especially in combination with ara-C against ALL) and/or pentostatin. Ribonucleotide reductase inhibitors are especially hydroxyurea or 2-hydroxy-1H-isoindole-1,3-dione derivatives, such as PL-1, PL-2, PL-3, PL-4, PL-5, PL-6, PL-7 or PL-8 mentioned in Nandy et al., Acta Oncologica, Vol. 33, No. 8, pp. 953-961 (1994).

The term "S-adenosylmethionine decarboxylase inhibitors" as used herein includes, but is not limited to the compounds disclosed in U.S. Pat. No. 5,461,076.

Also included are in particular those compounds, proteins or monoclonal antibodies of VEGF disclosed in WO 98/35958, e.g. 1-(4-chloroanilino)-4-(4-pyridylmethyl)phthalazine or a pharmaceutically acceptable salt thereof, e.g. the succinate, or in WO 00/09495, WO 00/27820, WO 00/59509, WO 98/11223, WO 00/27819 and EP 0 769 947; those as described by Prewett et al, Cancer Res, Vol. 59, pp. 5209-5218 (1999); Yuan et al., Proc Natl Acad Sci USA, Vol. 93, pp. 14765-14770 (1996); Zhu et al., Cancer Res, Vol. 58, pp. 3209-3214 (1998); and Mordenti et al., Toxicol Pathol, Vol. 27, No. 1, pp. 14-21 (1999); in WO 00/37502 and WO 94/10202; ANGIOSTATIN, described by O'Reilly et al., Cell, Vol. 79, pp. 315-328 (1994); ENDOSTATIN, described by O'Reilly et al., Cell, Vol. 88, pp. 277-285 (1997); anthranilic acid amides; ZD4190; ZD6474; SU5416; SU6668; bevacizumab; or anti-VEGF antibodies or anti-VEGF receptor antibodies, e.g. rhuMAb and RHUFab, VEGF aptamer e.g. Macugon; FLT-4 inhibitors, FLT-3 inhibitors, VEGFR-2 IgG1 antibody, Angiozyme (RPI 4610) and Bevacizumab (Avastin).

Photodynamic therapy as used herein refers to therapy which uses certain chemicals known as photosensitizing compounds to treat or prevent cancers. Examples of photodynamic therapy includes treatment with compounds, such as e.g. VISUDYNE and porfimer sodium.

Angiostatic steroids as used herein refers to compounds which block or inhibit angiogenesis, such as, e.g., anecortave, triamcinolone, hydrocortisone, 11-epihydrocotisol, cortexolone, 17-hydroxyprogesterone, corticosterone, desoxycorticosterone, testosterone, estrone and dexamethasone.

Implants containing corticosteroids refers to compounds, such as e.g. fluocinolone, dexamethasone.

"Other chemotherapeutic compounds" include, but are not limited to, plant alkaloids, hormonal compounds and antagonists; biological response modifiers, preferably lymphokines or interferons; antisense oligonucleotides or oligonucleotide derivatives; shRNA or siRNA; or miscellaneous compounds or compounds with other or unknown mechanism of action.

The structure of the active compounds identified by code nos., generic or trade names may be taken from the actual edition of the standard compendium "The Merck Index" or from databases, e.g. Patents International (e.g. IMS World Publications).

None of the quotations of references made within the present disclosure is to be understood as an admission that the references cited are prior art that would negatively affect the patentability of the present invention.

The compounds of the present invention may also be administered simultaneously, separately or sequentially in combination with one or more other suitable active agents selected from the following classes of agents: Anti IL-1 agents, e.g: Anakinra; anti cytokine and anti-cytokine receptor agents, e.g. anti IL-6 R Ab, anti IL-15 Ab, anti IL-17 Ab, anti IL-12 Ab; B-cell and T-cell modulating drugs, e.g. anti CD20 Ab; CTL4-Ig, disease-modifying anti-rheumatic agents (DMARDs), e.g. methotrexate, leflunamide, sulfasalazine; gold salts, penicillamine, hydroxychloroquine and chloroquine, azathioprine, glucocorticoids and non-steroidal anti-inflammatories (NSAIDs), e.g. cyclooxygenase inhibitors, selective COX-2 inhibitors, agents which modulate migration of immune cells, e.g. chemokine receptor antagonists, modulators of adhesion molecules, e.g. inhibitors of LFA-1, VLA-4.

The pharmaceutical composition or combination of the present invention can be in unit dosage of about 1-1000 mg of active ingredient(s) for a subject of about 50-70 kg, or about 1-500 mg or about 1-250 mg or about 1-150 mg or about 0.5-100 mg, or about 1-50 mg of active ingredients. In general, suitable daily dosages for oral administration are from about 0.1 to about 10 mg/kg. However, it will be understood by those of skill in the art that the therapeutically effective dosage of a compound, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

The above-cited dosage properties are demonstrable in vitro and in vivo tests using advantageously mammals, e.g., mice, rats, dogs, monkeys or isolated organs, tissues and preparations thereof. The compounds of the present invention can be applied in vitro in the form of solutions, e.g., aqueous solutions, and in vivo either enterally, parenterally, advantageously intravenously, e.g., as a suspension or in aqueous solution. The dosage in vitro may range between about $10^{-3}$ molar and $10^{-9}$ molar concentrations. A therapeutically effective amount in vivo may range depending on the route of administration, between about 0.1-500 mg/kg, or between about 1-100 mg/kg.

In general, a therapeutically effective amount of a compound of the present invention is administered to a patient in need of treatment. The term "a therapeutically effective amount" of a compound of the present invention refers to an amount of the compound of the present invention that will elicit the biological or medical response of a subject, for example, reduction or inhibition of an enzyme or a protein activity, or ameliorate symptoms, alleviate conditions, slow or delay disease progression, or prevent a disease, etc.

In yet another embodiment, a method for treating cancer in a subject is provided which comprises administering to a mammal in need of such treatment an effective amount of a compound of the present invention.

As used herein, the term "subject" refers to an animal. Typically the animal is a mammal. A subject also refers to for example, primates (e.g., humans, male or female), cows, sheep, goats, horses, dogs, cats, rabbits, rats, mice, fish, birds and the like. In certain embodiments, the subject is a primate. Preferably, the subject is a human.

As used herein, the term "inhibit", "inhibition" or "inhibiting" refers to the reduction or suppression of a given condition, symptom, or disorder, or disease, or a significant decrease in the baseline activity of a biological activity or process.

As used herein, the term "treat", "treating" or "treatment" of any disease or disorder, refers (i) to ameliorating the disease or disorder (i.e., slowing or arresting or reducing the development of the disease or at least one of the clinical symptoms thereof); (ii) to alleviating or ameliorating at least one physical parameter including those which may not be discernible by the patient; or (iii) to preventing or delaying the onset or development or progression of the disease or disorder. In general, the term "treating" or "treatment" describes the management and care of a patient for the purpose of combating the disease, condition, or disorder and includes the administration of a compound of the present invention to prevent the onset of the symptoms or complications, alleviating the symptoms or complications, or eliminating the disease, condition or disorder.

As used herein, a subject is "in need of" a treatment if such subject would benefit biologically, medically or in quality of life from such treatment.

Another aspect of the invention is a product comprising a compound of the present invention and at least one other therapeutic agent (or pharmaceutical agent) as a combined preparation for simultaneous, separate or sequential use in therapy to enhance apoptosis.

In the combination therapies of the invention, the compound of the present invention and the other therapeutic agent may be manufactured and/or formulated by the same or different manufacturers. Moreover, the compound of the present invention and the other therapeutic (or pharmaceutical agent) may be brought together into a combination therapy: (i) prior to release of the combination product to physicians (e.g. in the case of a kit comprising the compound of the invention and the other therapeutic agent); (ii) by the physician themselves (or under the guidance of the physician) shortly before administration; (iii) in the patient themselves, e.g. during sequential administration of the compound of the invention and the other therapeutic agent.

Accordingly, the invention provides the use of a compound of the present invention for treating a disease or condition by inhibiting the MAP kinase pathway, wherein the medicament is prepared for administration with another therapeutic agent. The invention also provides for the use of another therapeutic agent, wherein the medicament is administered as a combination of a compound of the present invention with the other therapeutic agent.

Embodiments of the present invention are illustrated by the following Examples. It is to be understood, however, that the embodiments of the invention are not limited to the specific details of these Examples, as other variations thereof will be known, or apparent in light of the instant disclosure, to one of ordinary skill in the art.

Process for Making Compounds of the Invention

The present invention also includes processes for the preparation of compounds of the invention. In the reactions described, it can be necessary to protect reactive functional groups, where these are desired in the final product, to avoid their unwanted participation in the reactions. Conventional protecting groups can be used in accordance with standard practice, for example, see T. W. Greene and P. G. M. Wuts in "Protective Groups in Organic Chemistry", John Wiley and Sons, 1991.

Individual enantiomers of the invention can be obtained from chiral separation of a racemate or can be individually synthesized from optically pure reagents using reaction scheme I:

Reaction Scheme I:

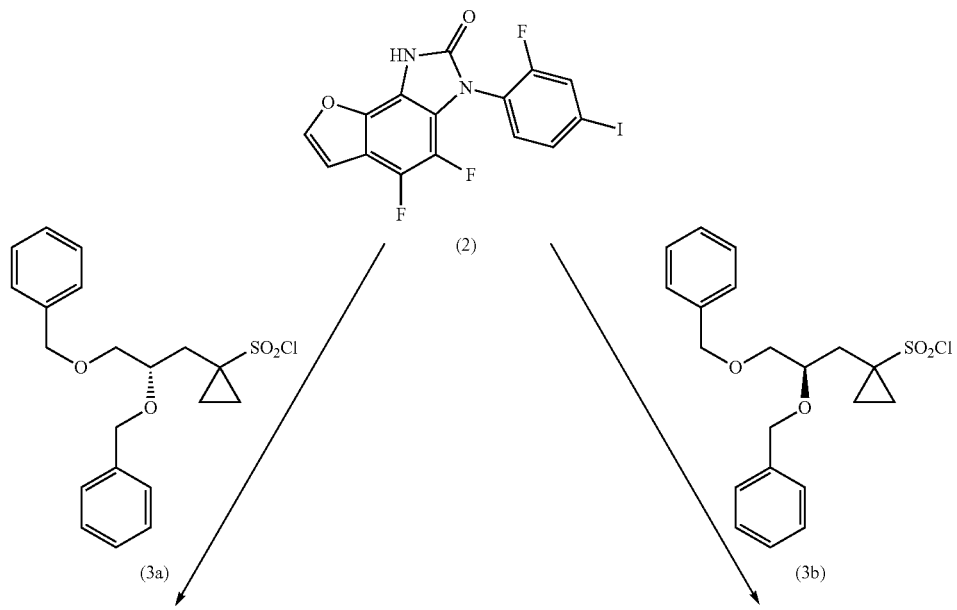

17   18
-continued
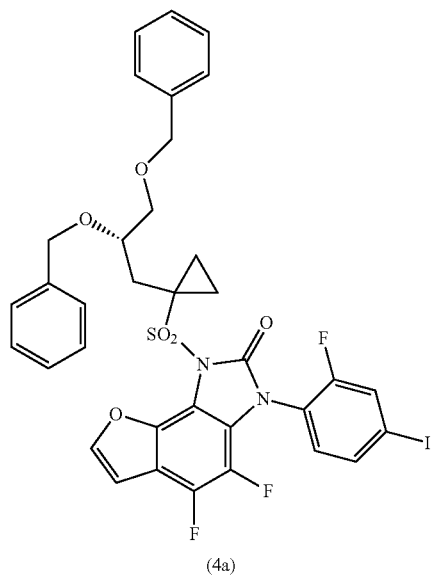
(4a)
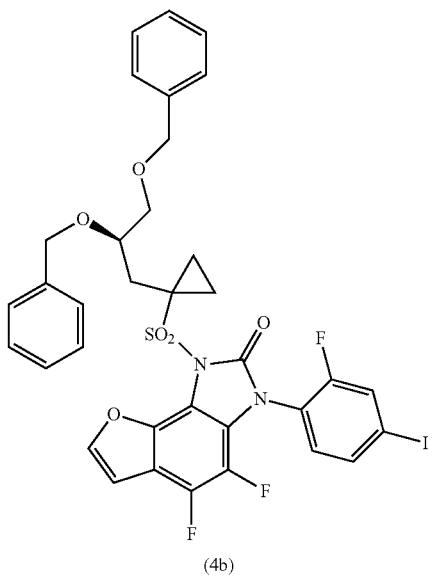
(4b)
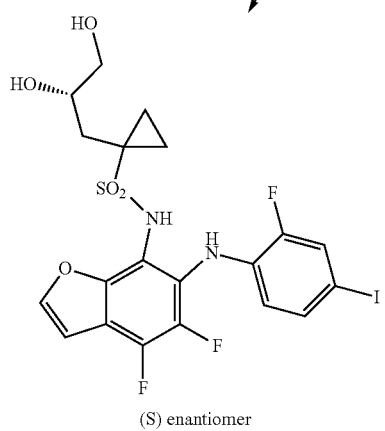
(5a)
(S) enantiomer
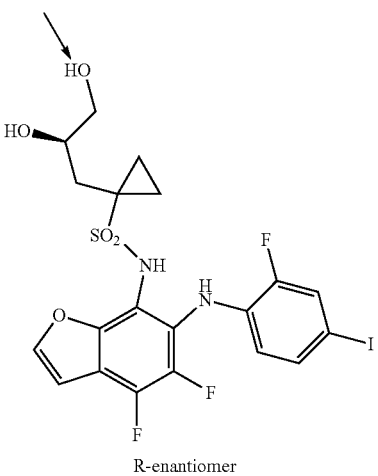
(5b)
R-enantiomer A compound of formula 4a can be prepared by reacting a compound of formula 2 with a compound of formula 3a in the presence of a suitable amine (for example, triethylamine, N,N-Diisopropylethylamine, Triisopropylamine, or the like), a suitable catalyst (for example, N,N-dimethylpyridin-4-amine, or the like) and a suitable solvent (for example, DCM, 1,2-dichloromethane, toluene, tetrahydrofuranyl, or the like). The reaction proceeds at a temperature of about 25° C. and can take up to about 12 hours to complete.

A compound of formula 5a can be prepared from a compound of formula 4a in the presence of a suitable base (for example, potassium trimethylsilanoate, or the like). The reaction proceeds at a temperature of about 25° C. and can take up to about 12 hours to complete.

The S-enantiomer can be prepared from a compound of formula 5a in the presence of a suitable Lewis acid (for example, trichlorborane, boron trifluoride, boron tribromide, or the like) and a suitable solvent (for example, dichloromethane, 1,2-dichloromethane, or the like). The reaction proceeds at a temperature of about 25° C. and can take up to about 1 hour to complete.

A compound of formula 4b can be prepared by reacting a compound of formula 2 with a compound of formula 3b in the presence of a suitable amine (for example, triethylamine, N,N-Diisopropylethylamine, Triisopropylamine or the like), a suitable catalyst (for example, N,N-dimethylpyridin-4-amine or the like) and a suitable solvent (for example, DCM, 1,2-dichloromethane, toluene, tetrahydrofuran, or the like). The reaction proceeds at a temperature of about 25° C. and can take up to about 12 hours to complete.

A compound of formula 5b can be prepared from a compound of formula 4b in the presence of a suitable base (for example, potassium trimethylsilanoate, or the like). The reaction proceeds at a temperature of about 25° C. and can take up to about 12 hours to complete.

The R-enantiomer can be prepared from a compound of formula 5b in the presence of a suitable Lewis acid(for example, trichlorborane boron trifluoride, boron tribromide, or the like) and a suitable solvent (for example, dichloromethane, 1,2-dichloromethane, or the like). The reaction proceeds at a temperature of about 25° C. and can take up to about 1 hour to complete.

EXAMPLES

The following abbreviations used herein below have the corresponding meanings: TEA (Triethylamine); EA (Ethyl acetate); MCC (Microcrystalline cellulose); DMAP (4-Dimethylaminopyridine); DCM (Dichloromethane); THF (Tetrahydrofuran); DMF (Dimethylformamide); LHMDS (lithium bis(trimethylsilyl)amide); CDI (1,1-Carbonyldiimidazole); PTSA (p-toluene sulfonic acid); RT (room temperature); TLC (thin layer chromatography); NMR (nuclear magnetic resonance); LC-MS (liquid chromatography-mass spectrometry); and HPLC (high pressure liquid chromatography or high performance liquid chromatography).

Preparation of Key Intermediates

Preparation of (2,3,5-trifluoro-N-(2-fluoro-4-iodophenyl)-6-nitroaniline

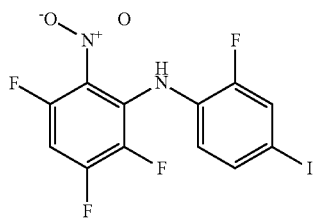

1.0M LHMDS in hexane (153 mL, 153 mmol) was added drop wise to a solution of 2-fluoro-4-iodoaniline (30.0 g, 128 mmol) in dry THF (600 mL) at −78° C. over a period of 30 minutes and the resulting mixture was stirred at −78° C. for a further 30 minutes. This was followed by the addition of 2,3,4,6-tetrafluoronitrobenzene (25 g, 128 mmol) in dry THF (150 mL) and stirring was continued for a further 1 hour at 20-40° C. The reaction was monitored by TLC (10% ethyl acetate in hexane). The reaction mixture was quenched with 2N HCl (100 mL), concentrated and the concentrate was partitioned between water (500 mL) and ethyl acetate (300 mL). The aqueous layer was washed with ethyl acetate (2×200 mL). The combined organic phase was washed with water, brine solution, dried over anhydrous $Na_2SO_4$ and concentrated to afford 38 g of the crude product. Purification by column chromatography on silica gel (0-5% ethyl acetate in hexane) afforded 31 g of the product (58.8% yield). LCMS: 95.5%, m/z=410.9 (M−1).

For large scale synthesis, 1,2,3,5-tetrafluoro-4-nitrobenzene was prepared by precooling a solution of $HNO_3$ (990 g) in $H_2SO_4$ (973 mL) and adding it into a cold solution of 1,2,3,5-tetrafluorobenzene (973.1 g) in $H_2SO_4$ (2920 mL) at a temperature between 0° C. and 10° C. over a 1.5 hour period. After the addition, the yellow solution was stirred at a temperature between 0° C. and 10° C. for 1 hour until analysis showed the reaction had gone to completion. The yellow solution was added in portions of water (9730 g) below 25° C. followed by the addition of DCM (9730 mL) to extract the aqueous layer. The DCM layer was then washed with water (10 L) twice. DCM was then concentrated to give a yellow oil. The oil was distilled under pressure (2.5 mbar) at 70° C. to −75° C. resulting in a yellow oil product (98% pure; 72.4% yield).

LiHMDS (1732 mL) was added to a solution of aniline in 2.5 L of THF at between −72° C. and −65° C. over 30 minutes. The resultant suspension was stirred at −70° C. for 30 minutes. A solution of nitrobenzene in 300 mL of THF was then added dropwise into the above suspension at between −75° C. and −70° C. over 1 hour and stirred at this temperature for a further 15 minutes. An additional 100 mL of LiHMDS was added at −70° C. and stirred at this temperature for 15 minutes. HPLC analysis revealed 23.4% of aniline, 6.6% nitrobenzene and 68.3% product. The solution was concentrated at 35° C. The resultant oil was then dissolved in 3 L of DCM followed by the addition of 2.5 L of water below 30° C. HCl (500 mL) was added (exothermic) and the solution was stirred for 15 minutes before separating. 2.5 L of water and 500 mL of HCl was added to the DCM layer and the wash was repeated 3 times. The DCM layers were concentrated to dryness and the batches added together to give about 1.4 kg of crude product. The solid was added to 20 L of hot heptanes solution (72° C.) and stirred for 1 hour. 200 g of active charcoal was added with stirring for 20 minutes. The suspension was hot filtered through MCC (2 kg) and rinsed with 5 L of hot heptanes (75° C.). The combined solution was then concentrated to 15 L and held overnight. The suspension was filtered to give 777 g of orange solid with 99% purity. The mother liquor was concentrated to about 5 L and stirred at room temperature and filtered to give an additional 120 g of orange solid. The overall yield was 46.8%. $^1$H NMR (DMSO-$d_6$, 400 MHz): δ 8.80 (s, 1H), 7.60-7.67 (m, 2H), 7.41 (d, 1H), 6.86 (t, 1H).

Preparation of 3-(2,2-diethoxyethoxy)-5,6-difluoro-N-(2-fluoro-4-iodophenyl)-2-nitroaniline

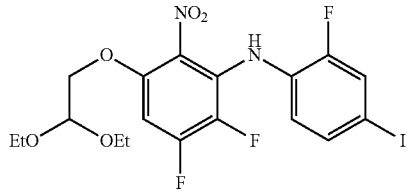 [SMILES: CCOC(COc1cc(F)c(F)c(Nc2ccc(I)cc2F)c1[N+](=O)[O-])OCC]

2,2-Diethoxy-ethanol (0.209 g, 1.2135 mmol) was added to a cooled suspension of NaH (0.034 g, 1.456 mmol) in THF (5 mL) at 0° C. and the resulting mixture was stirred for 30 minutes at RT. (2-Fluoro-4-iodo-phenyl)-(2,3,5-trifluoro-6-nitro-phenyl)-amine (0.5 g, 1.2135 mmol) in THF (10 mL) was added slowly to the reaction mass at 0° C. and stirring was continued for a further 15 minutes. The reaction mass was stirred overnight at room temperature. The reaction was monitored by TLC (20% ethyl acetate in hexane). The reaction mass was concentrated under reduced pressure and the concentrate was extracted with ethyl acetate. The organic layer was washed with water, brine solution, dried over sodium sulphate and concentrated under reduced pressure to afford the crude compound. Purification by column chromatography on silica gel (15% ethyl acetate in hexane) afforded 0.3 g of the product (47% yield). Two by products are isolated in this reaction. $^1$H NMR (CDCl$_3$, 300 MHz): δ 7.42 (d, 1H), 7.35 (d, 1H), 6.90 (bs, 1H), 6.58-6.68 (m, 2H), 4.58 (t, 1H), 4.15 (d, 2H), 3.51-3.80 (m, 4H), 1.22 (t, 6H).

For large scale synthesis, 2,2-diethoxyethanol was added dropwise into a suspension of 60% sodium hydride in 5 L of THF at 1-2° C. over 30 minutes and then stirred at 0-5° C. for 1.5 hours. A solution of 750 g of 2,3,5-trifluoro-N-(2-fluoro-4-iodophenyl)-6-nitroaniline in 2.25 L of THF was then added dropwise into the above suspension at 0-5° C. After the addition, the purple solution was stirred at room temperature for 2 days and 17 hours. HPLC analysis showed 4.1% remaining of 2,3,5-trifluoro-N-(2-fluoro-4-iodophenyl)-6-nitroaniline. 150 mL of water was added very slowly (gas generated) into the pre-cooled solution at 10° C. The solution was then concentrated to dryness. The resultant oil was then suspended in 5 L of heptanes and seeded with pure 3-(2,2-diethoxyethoxy)-5,6-difluoro-N-(2-fluoro-4-iodophenyl)-2-nitroaniline crystal and stirred for 30 minutes. After 1 hour of stirring, the precipitate was filtered and dried to yield 520 g (54.3%) of product with 96.4% purity. Further product was available in the mother liquor. $^1$H NMR (CDCl$_3$, 400 MHz): δ 7.42 (dd, 1H), 7.34 (d, 1H), 6.87 (bs, 1H), 6.56-6.67 (m, 2H), 4.79 (t, 1H), 4.06 (d, 2H), 3.74-3.82 (m, 2H), 3.59-3.66 (m, 2H); 1.24 (t, 6H).

(4,5-difluoro-7-nitro-benzofuran-6-yl)-(2-fluoro-4-iodo-phenyl)-amine

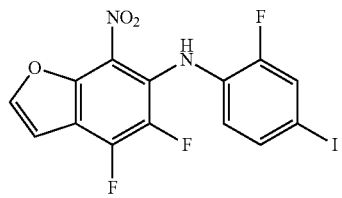 [SMILES: O=[N+]([O-])c1c(Nc2ccc(I)cc2F)c(F)c(F)c2ccoc12]

[3-(2,2-Diethoxy-ethoxy)-5,6-difluoro-2-nitro-phenyl]-(2-fluoro-4-iodo-phenyl)-amine (1 g, 1.9011 mmol) was dissolved in glacial acetic acid (10 mL) and concentrated under reduced pressure. The residue obtained was dissolved in dry DCM (10 mL) and cooled to 0° C. This was followed by the addition of BF$_3$.etherate (2.04 g, 14.476 mmol). The reaction was stirred for 12-16 hours at 20-40° C. The reaction was monitored by TLC (10% ethyl acetate in hexane). The reaction was quenched with 2N NaOH solution (15 mL), extracted with ethyl acetate (3×30 mL) and the combined organic extracts were dried over sodium sulphate, concentrated under reduced pressure to afford the crude compound. Purification by column chromatography on silica gel (5% ethyl acetate in hexane) afforded 0.260 g of the product (31% yield). $^1$H NMR (CDCl$_3$, 300 MHz): δ 8.95 (bs, 1H), 7.77 (d, 1H), 7.38-7.50 (1 dd, 1 d, 2H), 6.99 (d, 1H), 6.70-6.82 (m, 1H).

For scale up, a solution of 3-(2,2-diethoxyethoxy)-5,6-difluoro-N-(2-fluoro-4-iodophenyl)-2-nitroaniline (75 g) in 300 mL of DCM was added quickly into a solution of BF$_3$.ET$_2$O in 100 mL of DCM at 28-32° C. with further stirring for 15 minutes. After about 2 hours, analysis showed complete conversion. The solution was then quenched by 1N NaOH (dropwise) at a temperature below 30° C. to pH 10 before separating. DCM was then washed with water twice to a pH of about 7 and concentrated to dryness. 210 mL of MBTE was then added. The suspension was stirred for 30 minutes, filtered and dried to give 43 g of an orange solid. $^1$H NMR (CDCl$_3$, 400 MHz): δ 8.80 (bs, 1H), 7.75 (d, 1H), 7.48 (dd, 1H), 7.41 (d; 1H); 6.97 (d, 1H), 6.75-6.80 (m, 1H).

4,5-Difluoro-N6-(2-fluoro-4-iodo-phenyl)-benzofuran-6,7-diamine

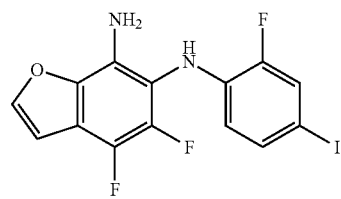 [SMILES: Nc1c(Nc2ccc(I)cc2F)c(F)c(F)c2ccoc12]

Concentrated HCl (1 mL) was added to a solution of (4,5-difluoro-7-nitro-benzofuran-6-yl)-(2-fluoro-4-iodo-phenyl)-amine (0.260 g, 0.599 mmol) in THF (5 mL) at 0° C. This was followed by the addition of zinc dust (0.179 g, 5.99 mmol) at 0° C. The reaction was stirred for 1 hour at 20-40° C. The reaction was monitored by TLC (20% ethyl acetate in hexane). The reaction was concentrated under reduced pressure and the concentrate was extracted with ethyl acetate (50 mL). The organic layer was washed with water, brine solution, dried over sodium sulphate and concentrated under reduced pressure to afford 0.240 g of the crude compound which was used for the next step without further purification. $^1$H NMR (CDCl$_3$, 300 MHz): δ 7.53 (d, 1H), 7.49 (dd, 1H), 7.20 (d, 1H), 6.00 (d, 1H), 6.20 (t, 1H), 5.42 (bs, 1H), 4.10 (bs, 2H).

For scale up synthesis, a solution of (4,5-difluoro-7-nitro-benzofuran-6-yl)-(2-fluoro-4-iodo-phenyl)-amine (165 g) and NH₄Cl in 2.5 L of THF and 2.5 L of water was cooled to between 0° C. and 5° C. Zinc dust was added (portionwise) at a temperature of less than 25° C. (exothermic during first half of addition) over 30 minutes. The addition of zinc dust resulted in a color change from yellow to dark purple and to pale yellow. Complete conversion was achieved with the addition of NH₄Cl (50 g) and zinc (60 g), followed by vigorous stirring for 20 minutes and a further 1.5 hours. Purity was 89.5%. The suspension was filtered and rinsed with 1 L of water and 1.5 L of THF. The combined solution was concentrated to remove THF (87.7% purity). 3 L of EA was added with stirring for 30 minutes. The layers were separated; the EA layer was washed with 2 L of water twice and then dried of MgSO₄. The EA was filtered and concentrated to dryness. The crude was used in the next step without further purification. ¹H NMR (CDCl₃, 400 MHz): δ 8.06 (d, 1H), 7.46 (dd, 1H), 7.40 (bs, 1H), 7.19 (d, 1H), 7.07 (d, 1H), 6.11 (t; 1H); 5.33 (bs, 1H).

4,5-Difluoro-3-(2-fluoro-4-iodophenyl)-1H-benzofuro[6,7-d]imidazol-2(3H)-one

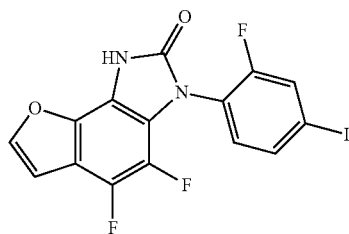 [SMILES: O=c1[nH]c2c3occc3c(F)c(F)c2n1-c1ccc(I)cc1F]

CDI (0.144 g, 0.891 mmol) was added to a solution of 4,5-difluoro-N6-(2-fluoro-4-iodo-phenyl)-benzofuran-6,7-diamine (0.240 g, 0.5940 mmol) in dry DCM (5 mL). The reaction mass was stirred for 12-16 hours at 20-40° C. The reaction was monitored by TLC (30% ethyl acetate in hexane). The reaction mass was concentrated under reduced pressure and the concentrate was extracted with ethyl acetate. The organic layer was washed with water, brine solution, dried over sodium sulphate and concentrated under reduced pressure to afford the crude compound. Purification by column chromatography on silica gel (30% ethyl acetate in hexane) afforded 0.180 g of the product (70% yield). ¹H NMR (DMSO-d₆,300 MHz): δ 12.15 (bs, 1H), 8.12 (d, 1H), 7.95 (dd, 1H), 7.79 (d, 1H), 7.50 (t, 1H), 7.21 (d, 1H).

For scale up synthesis, CDI(92.4 g, 570 mmol) was added to a solution of 4,5-difluoro-N6-(2-fluoro-4-iodo-phenyl)-benzofuran-6,7-diamine (153.6 g, 380.1 mmol) in 1500 mL of DCM at 0° C. The solution was then warmed to room temperature and stirred for approximately 48 hours. Analysis showed 0.3% remaining of 4,5-difluoro-N6-(2-fluoro-4-iodo-phenyl)-benzofuran-6,7-diamine with 86.1% purity. The solution was filtered to give crude gray solid with 96.4% purity. The crude was dissolved in 1.5 L of THF and then water (1.5 L) was added. The suspension was then concentrated to 1.7 L and filtered to give 87 g of product with 98.0% purity (53.2% yield). ¹H NMR (DMSO-d₆, 400 MHz): δ 12.29 (bs, 1H), 8.09 (d, 1H), 7.94 (dd, 1H), 7.76 (d, 1H), 7.47 (t, 1H), 7.19 (d, 1H).

1-(1-Allylcyclopropylsulfonyl)-4,5-difluoro-3-(2-fluoro-4-iodophenyl)-1H-benzofuro[6,7-d]imidazol-2(3H)-one

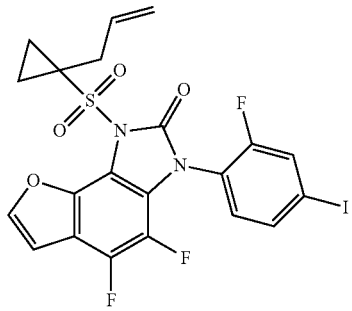

(I-34a)

TEA (0.2611 g, 2.581 mmol) was added to a solution of 4,5-difluoro-3-(2-fluoro-4-iodophenyl)-1H-benzofuro[6,7-d]imidazol-2(3H)-one0.37 g, 0.8604 mmol) in dry DCM (20 mL) at 0° C. This was followed by the addition of 1-allylcyclopropanesulfonyl chloride (0.229 g, 1.89 mmol) and catalytic amount of DMAP (10 mg). The reaction mass was stirred for 12 hours at 20-40° C. The reaction was monitored by TLC (20% ethyl acetate in hexane). The reaction mass was diluted with DCM (50 mL) and partitioned between water and DCM. The organic layer was washed with water, brine solution and concentrated under reduced pressure to afford the crude product. Purification by column chromatography on silica gel (20% ethyl acetate in hexane) afforded 0.228 g of the product (46% yield). ¹H NMR (CDCl₃, 300 MHz): δ 7.71 (dd, 3H), 7.30 (t, 1H), 7.00 (s, 1H), 5.56-5.57 (m, 1H), 4.90 (t, 2H), 2.70-2.80 (q, 2H), 1.90-2.05 (m, 2H), 1.10-1.19 (m, 2H). LCMS: 98.85%, m/z=574.4 (M+1). HPLC: 97.1%.

1-Allyl-N-(4,5-difluoro-6-(2-fluoro-4-iodophenylamino)benzofuran-7-yl)cyclopropane-1-sulfonamide

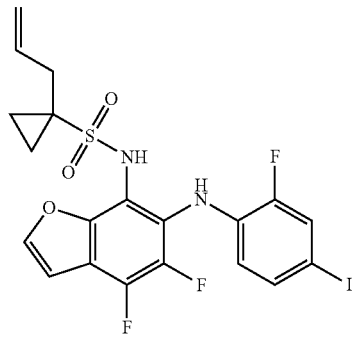 [SMILES: C=CCC1(S(=O)(=O)Nc2c(Nc3ccc(I)cc3F)c(F)c(F)c3ccoc23)CC1]

Potassium trimethyl silanolate (0.105 g, 0.82 mmol) was added to a solution of 1-(1-allylcyclopropylsulfonyl)-4,5-difluoro-3-(2-fluoro-4-iodophenyl)-1H-benzofuro[6,7-d]imidazol-2(3H)-one (0.230 g, 0.4108 mmol) in THF (5 mL) at 0° C. The reaction mass was stirred for 4 hours at 20-40° C. The reaction was monitored by TLC (10% ethyl acetate in hexane). The reaction mass was concentrated under reduced pressure and the concentrate was extracted with ethyl acetate. The organic layer was washed with water, brine solution, dried over sodium sulphate and concentrated under reduced pressure to afford the crude compound. Purification by column chromatography on silica gel (10% ethyl acetate in hexane) afforded 0.177 g of the product (78% yield). ¹H NMR (CDCl₃, 300 MHz): δ 7.54 (d, 1H), 7.40 (dd, 1H), 7.25 (s, 1H), 7.05 (bs, 1H), 6.99 (d, 1H), 6.32-6.39 (m, 1H), 6.22 (s, 1H), 5.65-5.75 (m, 1H), 5.19 (s, 1H), 5.10 (d, 1H), 2.88 (d, 2H), 1.15 (t, 2H), 0.75 (t, 2H). LCMS: 96.32%, m/z=548.8 (M+1). HPLC: 97.19%.

Isopropyl cyclopropanesulfonate

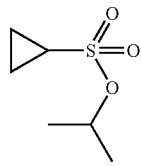

IPA (11 L) was added to pyridine (1850 g; 1890 mL) at 20° C. with stirring for 1 hour. The solution was cooled to between −10° C. and 2° C. and cyclopropane sulfonic chloride (1100 g) was added dropwise followed by stirring at this temperature for 70 hours. NMR analysis showed 85% of sulfonic chloride was consumed in the reaction. The reaction was cooled to 0° C. and NaOH (312 g) in water (600 mL) was added dropwise. The resultant product was concentrated to dryness and 45° C. and diluted with EtOAc (2750 mL), MTBE (1375 mL). The solution was stirred for 10 minutes and filtered. Heptane (1375 mL) was added, filtered and the filtrate was concentrated to dryness giving 1080 g of product as a red liquid (84% yield). ¹H NMR (CDCl₃, 400 MHz): δ 4.86 (m, 1H), 2.83 (m, 1H), 1.33 (d, 6H), 0.98-1.10 (m, 4H).

(S)-2-((benzyloxy)methyl)oxirane

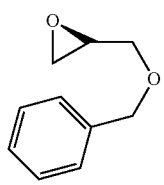

A slurry of NaH (267 g) and NaI (26.5 g) in DMF (3000 mL) was cooled to between −15° C. and −10° C. with ice-brine mixture. A solution of glycidol (480 g) in DMF (1000 mL) was added with stirring for 10 minutes. BnCl (745.5 g) in DMF (800 mL) was added (slightly exothermic) and the reaction was warmed to room temperature followed by stirring for approximately 16 hours. The solution was stirred for a further time period until HPLC analysis showed less than 1% of BnCl remained. The reaction was cooled to −5° C. and water (4 L) was added. MBTE (5 L) was added with stirring for 30 minutes. The organic and aqueous layers were separated and two additions of MBTE (5 L; 3.5 L) were used to extract the aqueous layer. The combined organic layer was washed with brine (1.8 L (×2)) and dried over Na₂SO₄ for 1 hour. The organic layer was concentrated to dryness, distilled under vacuum (5 mm Hg, 85° C.) to give the product as a yellow liquid (760 g). ¹H NMR (CDCl₃, 400 MHz): δ 7.27-7.37 (m, 5H), 4.51 (s, 2H), 3.74 (dd, 1H), 3.29 (dd, 1H), 3.14 (m, 1H), 2.72 (dd, 1H), 2.55 (dd, 1H).

(R)-isopropyl 1-(3-(benzyloxy)-2-hydroxypropyl)cyclopropane-1-sulfonate

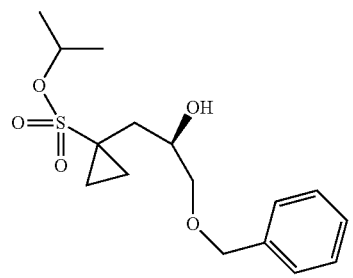 [SMILES: CC(C)OS(=O)(=O)C1(C[C@@H](O)COCc2ccccc2)CC1]

A solution of (S)-2-((benzyloxy)methyl)oxirane (507 g), HMPA (450 mL) and THF (4 L) was cooled with a dry ice-acetone bath to a temperature between −70° C. and −60° C. n-BuLi (1500 mL; 2.4 M) was added, dropwise, over 75 minutes. THF (450 g; 500 mL) was added to the reaction mixture, the temperature was raised to −20° C. gradually and the mixture was stirred for approximately 16 hours until HPLC analysis showed the reaction had gone to completion. The reaction mixture was cooled to −30° C. and water (300 mL) and concentrated aqueous HCl (300 mL) were added. The solution was concentrated to dryness. Water (2 L) was added and the product extracted twice with EtOAc (2.5 L (×2)). The combined organic layers were washed with water (2.5 L), brine (2 L), dried over Na₂SO₄ (500 g) and filtered. The filtrate was concentrated to dryness (at 45° C.) giving crude product as a red liquid (712 g; 75% yield).

(R)-isopropyl 1-(2,3-bis(benzyloxy)propyl)cyclopropane-1-sulfonate

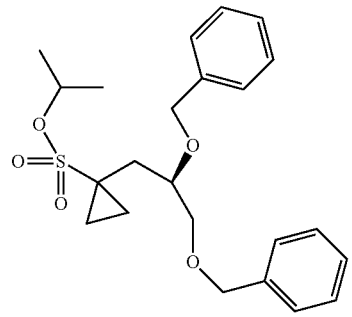 [SMILES: CC(C)OS(=O)(=O)C1(C[C@H](COCc2ccccc2)OCc2ccccc2)CC1]

Under a Nitrogen atmosphere was mixed NAH (91.5 g) in DMF (2 L) and (R)-isopropyl 1-(3-(benzyloxy)-2-hydroxypropyl)cyclopropane-1-sulfonate (715 g) in DMF (1 L) at a temperature between −5° C. and 5° C. for 140 minutes. After stirring for a further 5 minutes, NaI (5.1 g) was added. After BnCl (289.5 g) in DMF (300 mL) was added gradually, the reaction mixture was warmed slowly to room temperature and stirred for approximately 16 hours until HPLC analysis showed the reaction was complete. The reaction mixture was cooled to −5° C. and water (4 L) was added followed by MTBE (2 L (×2)) with stirring for 20 minutes. The organic layer was separated, washed with water (2 L (×2)), brine (2 L), dried over Na₂SO₄ and concentrated to give 830 g of product.

(R)-1-(2,3-bis(benzyloxy)propyl)cyclopropane-1-sulfonic acid

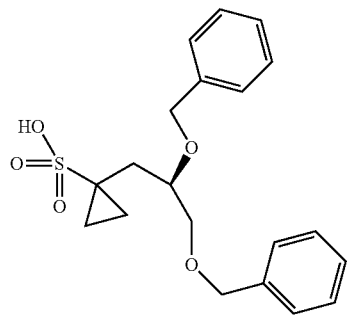 [SMILES: O=S(=O)(O)C1(C[C@H](COCc2ccccc2)OCc2ccccc2)CC1]

A mixture of (R)-isopropyl 1-(2,3-bis(benzyloxy)propyl)cyclopropane-1-sulfonate (460 g) and KSCN (170 g) in THF 2.2 L) and water (2.2 L) at 25° C. was refluxed for approximately 24 hours at 90° C. until HPLC analysis showed that the reaction had gone to completion. The reaction mixture was concentrated to about 2 L at 40° C. and extracted with MTBE (1.5 L (×3)). The organic layer was discarded and the aqueous layer was neutralized to pH 14 with KOH (30 g) in water (100 mL) and cooled to −5° C. The mixture was neutralized to a pH of between 2 and 3 with concentrated HCl (205 mL) and extracted with ETOAc (2 L (×2)). The combined organic layers was dried over Na₂SO₄ for approximately 16 hours, filtered and concentrated to dryness to give the product as a deep red oil (265 g).

(R)-1-(2,3-bis(benzyloxy)propyl)cyclopropane-1-sulfonyl chloride

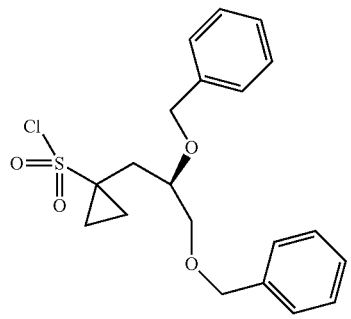 [SMILES: O=S(=O)(Cl)C1(C[C@H](COCc2ccccc2)OCc2ccccc2)CC1]

A mixture of (R)-1-(2,3-bis(benzyloxy)propyl)cyclopropane-1-sulfonic acid (630 g) and DMF (30 mL) in SOCl₂ (1.5 L) was refluxed for 2 hours until HPLC analysis showed the reaction had gone to completion. The reaction mixture was concentrated to dryness and the residue purified on silica gel chromoatography with eluent: heptane for 5 minutes, then IPAC: heptanes=1:30; heptanes 1:10 resulting in the product as a red oil (298.5 g; 52% yield; 95% purity). ¹H NMR (CDCl₃, 400 MHz): δ 7.34 (m, 10H), 4.68 (d, 1H), 4.56 (bs, 1H), 4.53 (d, 1H), 4.16 (m, 1H), 3.54-3.62 (m, 2H), 2.63 (dd, 1H), 2.01 (q, 1H), 1.52-1.81 (m, 3H), 1.16 (m, 1H), 2.22 (bs, 1H), 1.75 (t, 2H), 1.38-1.40 (m, 2H).

Example 1

1-(2,3-Dihydroxy-propyl)-cyclopropanesulfonic acid [4,5-difluoro-6-(2-fluoro-4-iodo-phenylamino)-benzofuran-7-yl]amide

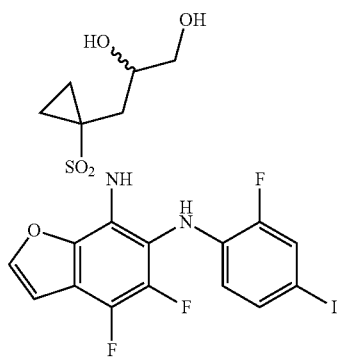

N-methyl morpholine oxide (0.035 g, 0.3041 mmol) was added to a solution of 1-allyl-cyclopropane sulfonic acid [4,5-difluoro-6-(2-fluoro-4-iodo-phenylamino)-benzofuran-7-yl]-amide (0.167 g, 0.3041 mmol) in THF (5 mL). This was followed by the addition of osmium tetroxide (0.0077 g, 0.03041 mmol) in water (1 mL). The reaction mass was stirred for 16 hours at 30-40° C. The reaction was monitored by TLC (10% methanol in chloroform). The reaction mass was partitioned between ethyl acetate (50 mL) and water. The organic layer was washed with water (3×50 mL), brine solution and concentrated under reduced pressure to afford the crude product. Purification by column chromatography on silica gel (5% methanol in chloroform) afforded 0.090 g of the product (50% yield). ¹H NMR (CDCl₃, 300 MHz): δ 7.69 (d, 2H), 7.40 (dd, 1H), 7.25 (s, 1H), 6.99 (d, 1H), 6.98 (bs, 1H), 6.38-6.40 (m, 1H), 4.25 (bs, 1H), 3.62 (dd, 2H), 3.32 (d, 1H), 2.55 (q, 1H), 2.22 (bs, 1H), 1.75 (t, 2H), 1.38-1.40 (m, 2H). LCMS: 99.49%, m/z=582.9 (M+1). HPLC: 95.29%.

For preparation of the enantiomers, the synthesis of 1-(2,3-dihydroxy-propyl)-cyclopropanesulfonic acid [4,5-difluoro-6-(2-fluoro-4-iodo-phenylamino)-benzofuran-7-yl]amide (Example 1) was scaled as follows: N-methyl morpholine oxide (0.32 g, 2.7272 mmol) was added to a solution of 1-allyl-cyclopropane sulfonic acid [4,5-difluoro-6-(2-fluoro-4-iodo-phenylamino)benzofuran-7-yl]amide (1.5 g, 2.7272 mmol) in THF (50 mL). This was followed by the addition of osmium tetroxide (0.695 g, 0.2737 mmol) in water (5 mL). The reaction mass was stirred overnight at room temperature. The reaction was monitored by TLC (10% methanol in chloroform). The reaction mass was partitioned between ethyl acetate (100 mL) and water (50 mL). The organic layer was washed with water (3×75 mL), brine solution and concentrated under reduced pressure to afford the crude product. Purification by column chromatography on silica gel (5% methanol in chloroform) afforded 0.9 g (56%, HPLC purity, 85%) of the product of racemic mixture which was further purified by preparative HPLC to afford the pure racemic compound 0.7 g (HPLC purity >98%).

The individual enantiomers were obtained by chiral column chromatography. 0.420 g of racemic 1-(2,3-dihydroxypropyl)-cyclopropanesulfonic acid [4,5-difluoro-6-(2-fluoro-4-iodo-phenylamino)-benzofuran-7-yl]amide was applied to a Chiralpak® AD-H™/02 semi prep column at 25° C. The mobile phase was composed of 80% hexane/10% IPA/10% MeOH with a 1 mL/minute flow rate. The diluent was IPA. The first eluted enantiomer, Example 1B, had a retention time of 10.971 minutes (0.185 g, 44%) and the second eluted enantiomer, Example 1A, had a retention time 14.961 minutes (0.175 g, 41%).

Alternatively, racemic 1-(2,3-dihydroxy-propyl)-cyclopropanesulfonic acid [4,5-difluoro-6-(2-fluoro-4-iodo-phenylamino)-benzofuran-7-yl]amide was applied to a Chiralpak® AD-H™/03 semi prep column at 25° C. The mobile phase was composed of 80% hexane/20% IPA with a 1 mL/minute flow rate. The diluent was ethanol. The first eluted enantiomer, Example 1A, had a retention time of 10.465 minutes (49%) and the second eluted enantiomer, Example 1B, had a retention time 13.535 minutes (46%).

The enantiomers were further purified by preparative HPLC to give Examples 1A and 1B with HPLC purity >99%.

The following synthetic description shows how (R)—N-(4,5-difluoro-6-((2-fluoro-4-iodophenyl)amino)benzofuran-7-yl)-1-(2,3-dihydroxypropyl)cyclopropane-1-sulfonamide was prepared:

(R)—N-(4,5-difluoro-6-((2-fluoro-4-iodophenyl)amino)benzofuran-7-yl)-1-(2,3-dihydroxypropyl)cyclopropane-1-sulfonamide

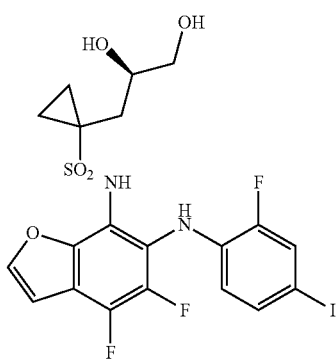

For large scale synthesis, a suspension of 4,5-difluoro-3-(2-fluoro-4-iodophenyl)-1H-benzofuro[6,7-d]imidazol-2(3H)-one (7 g; 16.275 mmol), (R)-1-(2,3-bis(benzyloxy)propyl)-cyclopropane-1-sulfonyl chloride (9.641 g), TEA (4.94 g) and a catalytic amount of DMAP (0.596 g) in DCM (75 mL) was stirred at room temperature for approximately 24 to 96 hours until HPLC analysis showed the reaction had gone to completion. The solution was then added to 1N HCl (60 mL) and stirred for 15 minutes and then separated. The DCM layer was dried over MgSO$_4$ and concentrated to dryness. The resultant (R)-1-(1-(2,3-bis(benzyloxy)propyl)cyclopropoxy)-4,5-difluoro-3-(2-fluoro-4-iodophenyl)-1H-benzofuro[6,7-d]imidazol-2(3H)-one compound with sulfur monoxide (1:1) was used in the following step without further purification.

Potassium trimethyl silanolate (165.5 g, 1.29 mol) was added to a solution of (R)-1-(1-(2,3-bis(benzyloxy)propyl)cyclopropoxy)-4,5-difluoro-3-(2-fluoro-4-iodophenyl)-1H-benzofuro[6,7-d]imidazol-2(3H)-one compound with sulfur monoxide (1:1) (251.2 g, 318.5 mmol) in THF (2.5 L) at 0° C.

The solution was warmed up to room temperature and stirred for 1-2 hours until HPLC analysis showed the reaction had gone to completion. Water (1.5 L) was added to the solution and the separated THF layer was concentrated to dryness. MTBE (2 L) was added to dissolve the oil and then washed with 2N aqueous NaOH solution (1 L) followed by washing with water (1.5 L). Active charcoal (50 g) was added into the MTBE solution for decolorization purpose and after the decolorization, the solution was concentrated to ~400 mL. Heptane (1.2 L) was added and the suspension was seeded with a pure (R)-1-(2,3-bis(benzyloxy)propyl)-N-(4,5-difluoro-6-((2-fluoro-4-iodophenyl)amino)benzofuran-7-yl) cyclopropane-1-sulfonamide crystal. The suspension was stirred at room temperature overnight and filtered, the white solid was dried to give 165 g of product with a 96% purity (68% overall yield).

To a solution of (R)-1-(2,3-bis(benzyloxy)propyl)-N-(4,5-difluoro-6-((2-fluoro-4-iodophenyl)amino)benzofuran-7-yl) cyclopropane-1-sulfonamide (140 g, 183.6 mmol) in DCM (700 mL) was added 1M BCl$_3$ solution in DCM (1.8 L, 1.84 mol) at −65-70° C. The mixture was stirred at −65~−70° C. for 30 minutes until HPLC analysis showed the reaction had gone to completion. The cold solution was added to 1N HCl solution (1.8 L) at below 15° C., stirred for 15 mins and separated. The DCM layer was washed with water (2 L), the brine (1.5 L). DCM layer was concentrated to ~250 mL and filtered to give white solid. The solid was dissolved in isobutyl acetate (240 mL) and heptane (500 mL) was added. The suspension was stirred overnight, filtered and dried to give 70 g of (R)—N-(4,5-difluoro-6-((2-fluoro-4-iodophenyl)amino)benzofuran-7-yl)-1-(2,3-dihydroxypropyl)cyclopropane-1-sulfonamide with 98.4% purity (65.5% yield, ee>99%).

Comparing the retention time under the same HPLC conditions (80% hexane/10% IPA/10% MeOH), the individually synthesized R-enantiomer has a retention time of 10.43 minutes, corresponding to the position of Example 1B.

Pharmacological Data

The inhibitory properties of compounds of present invention may be demonstrated using any one of the following test procedures:

A BRAF-MEK-ERK cascade assay is used to evaluate the effects of these compounds as inhibitors of the MAP kinase pathway. An enzymatic cascade assay is set up using recombinant human activated BRAF (V599E) kinase (Cat No. 14-557), human full length MEK1 kinase (Cat No. 14-706) and human full length active MAP Kinase 2/ERK2 (Cat No. 14-536) enzymes procured from Upstate. TR-FRET (Time resolved fluorescence resonance energy transfer) detection technology is used for the read out. The assay buffer solution contains 50 mM Tris pH 7.5, 10 mM MgCl2, 1 mM DTT, 0.01% Tween 20, 0.1 nM activated BRAF, 2 nM inactive MEK1, 10 nM inactive ERK2, 100 µM ATP and 500 nM long chain biotin-peptide substrate (LCB-FFKNIVTPRTPPP) in a 384 well format. The kinase reaction is stopped after 90 minutes with 10 mM EDTA and Lance detection mix (2 nM Eu-labeled phospho-serine/threonine antibody (Cat. No. AD0176-Perkin Elmer), 20 nM SA-APC (Cat No. CR130-100-Perkin Elmer) is added. The TR-FRET signal (Excitation at 340 nm, Emission at 615 nm and 665 nm) is read with 50 µs delay time on a Victor3 V fluorimeter. The data is calculated using the ratio of readings at 665 nm to 615 nm. The final concentration of DMSO is 2.5% in the assay. Compounds are screened at 10 µM concentration with pre-incubation of the enzymes in the presence of test compound for 45 minutes.

Each individual IC$_{50}$ is determined using a 10 point dose response curve generated by GraphPad Prism software Version 4 (San Diego, Calif., USA) using non linear regression curve fit for sigmoidal dose response (variable slope).

In this cascade assay, the IC50s of Examples 1, 1A and 1B were 2.1±0.58 nM, 2±0.25 nM and 1.6±0.1 nM respectively (mean±SEM, n=3).

An in-vitro MAP kinase assay is set up using activated MAP kinase 2/ERK2 (Cat. No. 14-550) obtained from Upstate. TR-FRET detection technology is used for the read out.

The assay buffer solution contains 50 mM Tris pH 7.5, 10 mM MgCl$_2$, 1 mM DTT, 0.01% Tween 20, 1 nM activated ERK2, 100 µM ATP and 500 nM long chain biotin-peptide substrate (LCB-FFKNIVTPRTPPP) in a 384 well format. The kinase reaction is stopped after 90 minutes with 10 mM EDTA and Lance detection mix (2 nM Eu-labeled phosphoserine/threonine antibody (Cat. No. AD0176-Perkin Elmer), 20 nM SA-APC (Cat. No. CR130-100-Perkin Elmer) is added. The TR-FRET signal (excitation at 340 nm, emission at 615 nm and 665 nm) is read with 50 µs delay time on Victor3 V fluorimeter. The data is calculated using the ratio of readings at 665 nm to 615 nm. The final concentration of DMSO is 2.5% in the assay. Compounds are screened at 10 µM concentration with pre-incubation of the enzymes in the presence of test compound for 45 minutes.

The radioactive filter binding assay is standardized using recombinant human activated BRAF (V599E) kinase (Cat No. 14-557) and kinase dead MEK1 (K97R) (Cat No. 14-737) procured from Upstate. The incorporation of 32P into MEK1 (K97R) by BRAF (V599E) is measured with final assay buffer conditions of 50 mM Tris pH 7.5, 10 mM MgCl2, 1 mM DTT, 100 mM sucrose, 100 µM sodium orthovanadate, 5 µM ATP and 2 µCi [γ32P] ATP and 500 mg MEK1 Kinase dead substrate. The enzymatic reaction is stopped after 120 minutes with 8N HCl (hydrochloric acid) and 1 mM ATP. The solution is spotted on P81 filter paper and washed 4 times with 0.75% orthophosphoric acid and lastly with acetone. The dried P81 filter papers are read in a Micro-beta Trilux scintillation counter. The final concentration of DMSO is 1% in the assay. Compounds are screened at 10 µM concentration with pre-incubation of the enzymes in the presence of test compound for 45 minutes.

These assays described above are fully detailed in Han, Shulin, et. al., Bioorganic & Medicinal Chemistry Letters (2005) 15, 5467-5473, and in Yeh, et. al., Clin Cancer Res (2007) 13 (5), 1576-1583.

The cell viability assay in A375 cells is set up in a 96-well plate format using XTT. XTT is a yellow tetrazolium salt that is cleaved to an orange formazan dye by the mitochondria of metabolically active cells. The procedure allows for rapid determination in a microtitre plate, to give reproducible and sensitive results.

A375 cells are grown in DMEM media containing 10% FBS and 1 mM sodium pyruvate. Cells are trypsinized and seeded at 1000 cells/well. After allowing the cells to adhere overnight, compound is added to the wells at the following final concentrations: 10, 3, 1, 0.3, 0.1, 0.03, 0.01, 0.001, and 0.0001 µM. The assay is set up in triplicates for each concentration. DMSO concentrations are kept at 0.5%/well. Three days after compound addition, the XTT assay is performed. Wells are washed once with PBS. 100 µL of DMEM media without phenol red or FBS is added to each well. A working solution of XTT containing 1 mg/ml XTT and 100 µL of PMS (stock concentration 0.383 mg/ml) per 5 ml is prepared. 50 µL of the working solution of XTT is added to each well. Absorbance of the plate is read at 465 nm using a Spectramax 190 (Molecular Devices). The absorbance from wells with media and XTT alone, but without cells is considered the blank and subtracted from readings from all wells.

The cell viability assay is further described in Scudiero, et. al., Cancer Research (1988) 48, 4827-4833; Weislow, et. al., J. Natl. Cancer Institute, (1989) 81, 577-586; and Roehm, et. al., J. Immunol. Methods [1991]142:257-265.

Percentage viability is calculated considering the blank subtracted value from wells treated with DMSO alone as 100% viable. GI$_{50}$ values are calculated using Graphpad Prism, using non-linear regression curve fit for sigmoidal dose response (variable slope). Compounds of the invention were evaluated in this cell viability assay. Example 1A has a GI$_{50}$ of 13.4 nM and Example 1B has a GI$_{50}$ of 29.6 nM, while Example 1 has a GI$_{50}$ of 17.6 nM.

A375 P-Erk (In-Cell-Western):

Human melanoma A375 cells were seeded at 50,000 cells per well in 100 µl growth medium in Costar 96 well black clear bottom plates and placed at 37° C./5% CO$_2$ over night. Test compounds were diluted in DMSO to generate a concentration curve. A 5 mM stock was used for the highest concentration at 500 times; to yield a final concentration of 10 µM with 3-fold dilutions down to 0.0001 µM. 1 µl of diluted compound was added to 500 µl cell culture media and mixed well. Media was removed from cells and 200 µl of media containing compound was added. Cells were treated for 3 hrs with compound at 37° C., 5% CO$_2$.

After the compound incubation, cells were washed once with PBS (Mg$^{++}$,Ca$^{++}$) and fixed in 4% paraformaldehyde/PBS for 1 hr at room temperature. Following fixation, cells were washed three times with PBS/0.1% TritonX-100 (PBST), and then blocked with 5% skimmed milk/PBST, for 1-2 hr. 50 µL per well primary antibody was added (rabbit-anti-phospho-ERK1/2) at 1:500 in 5% skimmed milk/PBST and incubated overnight at 4° C. Cells were washed four times with 100 µl DELFIA wash buffer and 50 µL per well secondary antibody was added (DELFIA-EU-N-1-labeled anti-rabbit antibody) at 1:3000 in DELFIA assay buffer and incubated for 2 hr at room temperature in the dark (covered). Cells were washed 4× with 100 µl DELFIA wash buffer. 50 µL per well Wallac-DELFIA enhancement solution was added. Plates were shaken at room temperature for 20 min and then read on the Perkin Elmer Victor3v reader on the Europium setting (emission/excitation of 615/340 nm).

EC$_{50}$ values were calculated using DMSO diluent values as 0% inhibition and counts of the highest tested concentration of the reference inhibitor as 100% inhibition. All the concentrations along with DMSO were done in triplicates. The EC$_{50}$ of Example 1A is 6.4 nM compared with 15.6 nM for Example 1B and 12.2 nM for Example 1.

Pharmacokinetics in Athymic Nude Rats

For pharmacokinetics studies, the following parameters were calculated by non-compartmental regression analysis using Winnonlin 5.0 software (Pharsight, Mountain View, Calif., USA): half life in plasma ($t_{1/2term}$); plasma clearance (CL); plasma maximum concentration (Cmax); plasma area-under-the-concentration-time-curve (AUC); and percent oral bioavailability (F %).

Pharmacokinetics parameters in rat for some compounds of the invention are given in the table below:

| | i.v. (0.5 mg/kg) | | | | p.o. (3 mg/kg) | | |
|---|---|---|---|---|---|---|---|
| Compound | AUC μg·hr/mL | Cl mL/hr/kg | $T_{1/2}$ hr | Vd mL/kg | Cmax μg/mL | AUC μg·hr/mL | % F |
| Example-1 | 70 ± 9 | 7.6 ± 0.9 | 15.6 ± 1.7 | 170 ± 6 | 9.8 ± 0.7 | 365 ± 45 | 87 |
| Example-1A | 126 ± 3 | 4.0 ± 0.1 | 19.9 ± 0.8 | 110 ± 6 | 25.6 ± 0.7 | 994 ± 30 | 132 |
| Example-1B | 100 ± 14 | 5.2 ± 0.7 | 17.1 ± 1.8 | 125 ± 6 | 25.2 ± 2.7 | 752 ± 84 | 126 |

Examples 1A and 1B show improved PK-parameters compared to Example 1 (one-way analysis of variance).

A375 B-RafV600E Human Melanoma Model in Rat—PK-PD Experiment:

A375 cells were thawed using a 37° C. water bath. Cells were transferred to a tube containing 10 mls of warm DMEM medium. The tube was centrifuged for 5 minutes at 1200 rpm and the supernatant was discarded. The cell pellet was re-suspended and transferred to a 75 $cm^2$ tissue culture flask containing 15 mls of medium and cultured at 37° C. in a 5% $CO_2$ incubator.

On the day of the cells implantation, cells were harvested (about 85% confluent), and re-suspended in cold medium containing 4 mg/ml of matrigel. This cell suspension was injected, subcutaneously, to athymic-nude pre-irradiated (500 rads) rats. Ten million cells (injection volume, 200 μL) were injected, subcutaneously, into the right flank region of the rats 24 hours after irradiation. Tumor bearing rats were randomized when the tumor volume reached approximately 500 $mm^3$ after about 15 to 20 days. Three rats were used for each time point.

Rats were treated orally with a single dose of 10, 30 and 60 mg/kg p.o. of Example 1A and 30 mg/kg of Example 1B. Plasma and tumor samples were taken at 4, 12, 24 and 36 hours, post dosing. The mRNA expression levels of two direct target genes of MEK substrate P-Erk (DUSP6 and SPRY4) and an indirect target (BMF) can be measured. Upon treatment with MEK inhibitors, these genes have been shown to be regulated in a dose-dependent manner in tumor cell lines grown in vitro and in vivo. The tumor samples were pulverized, extracted and studied for expression of the transcription factor DUSP6 using a real time quantitative PCR.

Surprisingly, a two-way analysis of variance showed that Example-1A was significantly more effective than Example-1B at lowering levels of DUSP-6 at 12 h and 24 h (p=0.003 and p=0.006, respectively).

The invention claimed is:

1. A compound which is (S)—N-(4,5-difluoro-6-((2-fluoro-4-iodophenyl)amino)benzofuran-7-yl)-1-(2,3-dihydroxypropyl)cyclopropane-1-sulfonamide or the pharmaceutically acceptable salt thereof 2. A pharmaceutical composition comprising a compound of claim 1 admixed with at least one pharmaceutically acceptable excipient.

3. The pharmaceutical composition of claim 2, wherein the excipient is selected from the group consisting of corn starch, potato starch, tapioca starch, starch paste, pre-gelatinized starch, sugars, gelatin, natural gums, synthetic gums, sodium alginate, alginic acid, tragacanth, guar gum, cellulose, ethyl cellulose, cellulose acetate, carboxymethyl cellulose calcium, sodium carboxymethylcellulose, methyl cellulose, hydroxypropyl methylcellulose, microcrystalline cellulose, magnesium aluminum silicate, polyvinyl pyrrolidone, talc, calcium carbonate, powdered cellulose, dextrates, kaolin, mannitol, silicic acid, sorbitol, agar-agar, sodium carbonate, croscarmellose sodium, crospovidone, polacrilin potassium, sodium starch glycolate, clays, sodium stearate, calcium stearate, magnesium stearate, stearic acid, mineral oil, light mineral oil, glycerin, sorbitol, mannitol, polyethylene glycol, other glycols, sodium lauryl sulfate, hydrogenated vegetable oil, peanut oil, cottonseed oil, sunflower oil, sesame oil, olive oil, corn oil, soybean oil, zinc stearate, sodium oleate, ethyl oleate, ethyl laureate, silica, and combinations thereof 4. The pharmaceutical composition of claim 2, further comprising an additional therapeutic agent.

5. The pharmaceutical composition of claim 4, wherein the additional therapeutic agent is selected from an anticancer compound, an analgesic, an antiemetic, an antidepressant, and an anti-inflammatory agent.

6. A method to treat melanoma, comprising administering to a subject in need of such treatment an effective amount of a compound claim 1 or a pharmaceutical composition of claim 2.

7. The method of claim 6, further comprising administering to the subject an additional therapeutic agent.

8. The method of claim 7, wherein the additional therapeutic agent comprises an anticancer drug, a pain medication, an antiemetic, an antidepressant or an anti-inflammatory agent.

9. The method of claim 8, wherein the additional therapeutic agent is a MEK inhibitor or an inhibitor of RAF, mTOR, HSP90, AKT, PI3K, CDK9, PAK, Protein Kinase C, a MAP kinase, a MAPK Kinase, or ERK.

10. The method of claim 9, wherein the MEK inhibitor is selected from: AS703026; MSC1936369B; GSK1120212; AZD6244; PD-0325901; ARRY-438162; RDEA119; GDC0941; GDC0973; TAK-733; R05126766; and XL-518.

11. The method of claim 10, wherein the additional therapeutic agent is administered to the subject concurrently with the compound.

12. A process for the manufacture of (R)—N-(4,5-difluoro-6-((2-fluoro-4-iodophenyl)amino)benzofuran-7-yl)-1-(2,3-dihydroxypropyl)cyclopropane-1-sulfonamide by: (i) reacting 4,5-difluoro-3-(2-fluoro-4-iodophenyl)-1H-benzofuro[6,7-d]imidazol-2(3H)-one with (R)-1-(2,3-bis(benzyloxy)propyl)cyclopropane-1-sulfonyl chloride to form (R)-1-(1-(2,3-bis(benzyloxy)propyl)cyclopropoxy)-4,5-difluoro-3-(2-fluoro-4-iodophenyl)-1H-benzofuro[6,7-d]imidazol-2(3H)-one compound with sulfur monoxide (1:1) in the presence of a base selected from triethylamine N,N-Diisopropyiethylamine and triisopropylamine; (ii) reacting (R)-1-(1-(2,3-bis(benzyloxy)propyl)cyclopropoxy)-4,5-difluoro-3-(2-fluoro-4-iodophenyl)-1H-benzofuro[6,7-d]imidazol-2(3H)-one in the presence of potassium trimethylsilanoate to form (R)-7-((1-(2,3-bis(benzyloxy)propyl)cyclopropoxy)amino)-4,5-difluoro-N-(2-fluoro-4-iodophenyl)benzofuran-6-amine compound with sulfur monoxide (1:1); and (iii) reacting (R)-7-((1-(2,3-bis(benzyloxy)propyl)cyclopropoxy)amino)-4,5-difluoro-N-(2-fluoro-4-iodophenyl)benzofuran-6-amine compound with sulfur monoxide (1:1) in the presence of a suitable catalyst selected from trichlorborane, boron trifluoride and boron tribromide to form (R)-N-(4,5-difluoro-6-((2-fluoro-4-iodophenyl)amino)benzofuran-7-yl)-1-(2,3-dihydroxypropyl)cyclopropane-1-sulfonamide.

* * * * *